(12) United States Patent
Yamaoka et al.

(10) Patent No.: US 7,780,828 B2
(45) Date of Patent: Aug. 24, 2010

(54) ANALYTICAL INSTRUMENT HAVING IMPROVED ARRANGEMENT OF REAGENT SECTION AND ANALYTICAL METHOD

(75) Inventors: Hideaki Yamaoka, Kyoto (JP); Kenji Nagakawa, Kyoto (JP); Mitsuhiro Hoshijima, Kyoto (JP); Sadaaki Kimura, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 874 days.

(21) Appl. No.: 10/585,295

(22) PCT Filed: Jan. 7, 2005

(86) PCT No.: PCT/JP2005/000153

§ 371 (c)(1),
(2), (4) Date: Jul. 6, 2006

(87) PCT Pub. No.: WO2005/066638

PCT Pub. Date: Jul. 21, 2005

(65) Prior Publication Data

US 2009/0017483 A1 Jan. 15, 2009

(30) Foreign Application Priority Data

Jan. 7, 2004 (JP) ............................ 2004-001746

(51) Int. Cl.
*G01N 27/327* (2006.01)

(52) U.S. Cl. ............................. 204/403.04; 204/403.11

(58) Field of Classification Search .................. 204/403.01–403.15; 205/777.5, 778, 792; 422/55–58
See application file for complete search history.

(56) References Cited

U.S. PATENT DOCUMENTS

| | | | |
|---|---|---|---|
| 5,320,732 A | 6/1994 | Nankai et al. | |
| 6,261,519 B1 * | 7/2001 | Harding et al. | 422/58 |
| 6,436,255 B2 * | 8/2002 | Yamamoto et al. | 204/403.1 |
| 6,471,839 B1 * | 10/2002 | Yamamoto et al. | 204/403.06 |
| 6,541,861 B2 | 4/2003 | Higashi et al. | |
| 6,740,215 B1 * | 5/2004 | Nakaminami et al. | 204/403.14 |
| 6,821,410 B2 | 11/2004 | Watanabe et al. | |
| 7,390,391 B2 * | 6/2008 | Nagakawa et al. | 205/777.5 |
| 2004/0142406 A1 | 7/2004 | Nagakawa et al. | |
| 2004/0173458 A1 | 9/2004 | Noda et al. | |
| 2005/0036906 A1 | 2/2005 | Nakahara et al. | |

(Continued)

FOREIGN PATENT DOCUMENTS

EP 1 615 031 11/2006

(Continued)

*Primary Examiner*—Alex Noguerola
(74) *Attorney, Agent, or Firm*—Hamre, Schumann, Mueller & Larson, P.C.

(57) ABSTRACT

The present invention relates to an analytical instrument (1) which includes a flow path (5) for moving a sample containing blood cells, an introduction port (50) for introducing the sample into the flow path (5), a reagent portion (51) arranged in the flow path (5), and an electron detection medium (52) for obtaining information necessary for analyzing an analysis target component contained in the sample in relation with an amount of electrons transferred. The reagent portion (51) contains an electron mediator for supplying an electron taken from the analysis target component in the sample to the electron detection medium (52), and at least part of the reagent portion is positioned adjacent to the introduction port (50).

22 Claims, 17 Drawing Sheets

U.S. PATENT DOCUMENTS

2007/0053790 A1 * 3/2007 Nagakawa et al. ............ 422/55

FOREIGN PATENT DOCUMENTS

| GB | 2254436 A * | 10/1992 |
| JP | 4-357449 | 12/1992 |
| JP | 2002-175699 | 6/2002 |
| JP | 2002-333420 | 11/2002 |
| JP | 2004-101519 | 4/2004 |
| WO | WO 02/33407 | 4/2002 |
| WO | WO 03/008956 | 1/2003 |
| WO | WO 03/057905 | 7/2003 |
| WO | WO 2004/092725 | 10/2004 |

* cited by examiner

ANALYTICAL INSTRUMENT HAVING IMPROVED ARRANGEMENT OF REAGENT SECTION AND ANALYTICAL METHOD

This application is a 371 of PCT/JP2005/000153, filed Jun. 7, 2005, which claims foreign priority from Japanese application 2004-001746, field Jan. 7, 2004.

TECHNICAL FIELD

The present invention relates to a technique for analyzing a particular component contained in a sample, in particular to a technique for measuring the glucose level in blood.

BACKGROUND ART

Examples of glucose sensors dealing with a sample of whole blood include sensors that utilize a colorimetric method or an electrode method (see Patent Documents 1 and 2, for example). In both of the above-described two techniques, the glucose level is determined by supplying electrons taken from glucose to an electron detection medium (color former or electrode) and grasping, from the outside of the glucose sensor, the amount of electrons supplied. Generally, the glucose sensor is designed to take electrons from glucose by oxidoreductase and supplying the electrons to the electron detection medium via an electron mediator.

It is known that, in measuring the glucose level using whole blood, the measurement result is influenced by the blood cell concentration (hematocrit), and a high hematocrit causes the measurement result to be lower than the actual glucose level. As one of the causes of such a phenomenon, it has been pointed out that to take electrons from the glucose existing in blood cells requires longer time than to take electrons from the glucose existing in blood serum (blood plasma). Specifically, electrons can be quickly taken from the glucose existing in blood serum (blood plasma) by oxidoreductase. On the other hand, electrons existing in the glucose in blood cells cannot be taken out until the glucose is transferred to the blood serum (blood plasma). Further, the transfer of glucose from blood cells to blood serum (blood plasma) is not the simple diffusion due to the difference of glucose level between inside and outside of blood cells but the facilitated diffusion which depends on the glucose transmission ability of blood cell membranes. Thus, the rate of diffusion of glucose to the outside of blood cells follows the Michaelis-Menten equation and has a limit value. Therefore, when the difference of glucose level between inside and outside of the blood cells exceeds a predetermined value, the rate of diffusion of glucose to the outside of blood cells becomes a constant value. Therefore, in a system in whole blood in which an oxidoreductase, an electron mediator and an electron detection medium coexist, although electrons taken from the glucose existing in blood serum (blood plasma) are immediately supplied to the electron detection medium, it takes time to diffuse the glucose of the amount corresponding to the supplied amount to the outside of the blood cells. As a result, the electrons taken from the glucose originally existed in blood cells are supplied to the electron detection medium later as compared with the glucose originally existed in the blood serum (blood plasma). Such a delay is large in the whole blood with high blood cell concentration. Therefore, in a stage after a certain period has elapsed from the sample supply, the ratio of glucose transferred from blood cells to blood serum (blood plasma) may be smaller in the whole blood having a high blood cell concentration than in the whole blood having a low blood cell concentration even when the blood glucose level is the same.

Recently, the measurement time tends to be shortened, and novel oxidoreductase and electron mediator are sought for the purpose. In such a condition, the glucose existing in the blood serum (blood plasma) is consumed in a short time. On the other hand, the rate of transfer of glucose from blood cells does not change greatly, because the diffusion of glucose from the blood cells to the blood serum (blood plasma) depends on the glucose transmission ability of blood cell membranes. Therefore, in whole blood with high hematocrit, as the measurement time is shortened, the ratio of glucose which can be transferred from blood cells to blood serum (blood plasma) within the measurement time decreases, and the above-mentioned low-value problem becomes more significant.

Moreover, the oxidoreductase and the electron mediator are retained in the glucose sensor as a reagent portion in a solid state soluble in blood, for example (See Patent Document 3, for example). Therefore, as the measurement time is shortened, the influence of the solubility of the reagent portion on the measurement accuracy increases. When the reagent portion has poor solubility, the oxidoreductase and the electron mediator do not disperse uniformly in the liquid phase reaction system established when the reagent portion is dissolved by the blood, which causes variations in the measurement results. Such variations in the measurement results are remarkable when the glucose level in the blood is low.

Patent Document 1: JP-A-2002-175699
Patent Document 2: JP-B-8-10208
Patent Document 3: JP-A-2004-101519

DISCLOSURE OF THE INVENTION

An object of the present invention is, in analyzing a sample containing blood cells (e.g. in measuring the glucose level in blood), to suppress the influence of the blood cell concentration and to prevent the low value problem especially in the case of a sample having a high blood cell concentration.

Another object of the present invention is to reduce the variations of measurement results caused when the measurement time is shortened and to enhance the reproducibility of measurements particularly in a low concentration range.

According to a first aspect of the present invention, there is provided an analytical instrument having improved arrangement of reagent portion. The analytical instrument comprises a flow path for moving a sample (e.g. blood) containing blood cells, an introduction port for introducing the sample into the flow path, a reagent portion arranged in the flow path, and an electron detection medium for obtaining information necessary for analyzing an analysis target component (e.g. glucose) contained in the sample in relation with an amount of electrons transferred. The reagent portion contains an electron mediator for supplying an electron taken from the analysis target component in the sample to the electron detection medium, and at least part of the reagent portion is positioned adjacent to the introduction port.

For instance, the reagent portion is arranged upstream from the electron detection medium in the direction of flow of the sample while being separated from the electron detection medium. In this case, it is preferable that the reagent portion is in a solid state and dissolves when the sample is supplied to the flow path.

Preferably, the distance between the reagent portion and the electron detection medium is so set that, when the sample contains the analysis target component in the maximum amount of a predetermined detection range, electron transfer from the maximum amount of analysis target component to the electron mediator is substantially completed before the electron mediator becomes able to supply electrons to the electron detection medium.

Preferably, the content of the electron mediator in the reagent portion is so set that, when the sample contains the analysis target component in the maximum amount of a predetermined detection range, the electron mediator can receive all the electrons taken from the maximum amount of analysis target component.

The electron detection medium may contain a color former. In this case, it is preferable that the electron detection medium is provided by causing a porous body which is sparingly soluble in the sample to support the color former. Typical examples of porous body include gels such as polyacrylamide gel or polyvinyl alcohol gel, while examples of color former include: MTT(3-(4,5-Dimethyl-2-thiazolyl)-2,5-diphenyl-2H-tetrazolium bromide); INT(2-(4-Iodophenyl)-3-(4-nitrophenyl)-5-phenyl-2H-tetrazolium chloride); WST-4(2-(4-Iodophenyl)-3-(2,4-dinitrophenyl)-5-(2,4-disulfophenyl)-2H-tetrazolium, monosodium salt); and 4AA(4-Aminoantipyrine).

The electron detection medium may comprise a conductor. The conductor may be one which is utilized for applying voltage to the electron mediator when the sample is supplied to the flow path.

The reagent portion may contain an oxidoreductase for taking an electron from the analysis target component contained in the sample and supplying the electron to the electron mediator. The oxidoreductase may be retained on the analytical tool as an additional reagent portion provided separately from the reagent portion. Preferably, in this case, the additional reagent portion is arranged between the reagent portion and the electron detection medium in the direction of flow of the sample in the flow path. For instance, the additional reagent portion is in a solid state and dissolves when the sample is supplied to the flow path.

According to a second aspect of the present invention, there is provided an analytical instrument comprising: a flow path for moving a sample containing blood cells; an introduction port for introducing the sample into the flow path; an electron detection medium for obtaining information necessary for analyzing an analysis target component contained in the sample in relation with an amount of electrons transferred, the electron detection medium comprising a porous body which is sparingly soluble in the sample and in which a color former is supported; an electron mediator layer which contains an electron mediator for supplying an electron taken from the analysis target component contained in the sample to the electron detection medium and which dissolves when the sample is supplied to the flow path; and an oxidoreductase layer which contains an oxidoreductase for taking an electron from the analysis target component contained in the sample and supplying the electron to the electron mediator and which dissolves when the sample is supplied to the flow path. The electron mediator layer, the oxidoreductase layer and the electron detection medium are aligned in the flow path in mentioned order from an upstream side in the direction of flow of the sample.

For instance, the reagent portion (the electron mediator layer) may be larger than the additional reagent portion (oxidoreductase layer) in area in plan view and in length in the direction of flow of the sample or smaller in thickness (e.g. 15 to 80% of the thickness of the oxidoreductase layer).

The reagent portion (the electron mediator layer) may have a length which accounts for 50 to 90% of the distance from the sample introduction port to an end of the additional reagent portion (the oxidoreductase layer) on the sample introduction port side. The reagent portion (the electron mediator layer) may have an area in plan view which is 1.5 to 10 times the area in plan view of the electron detection medium in the flow path.

As the electron mediator in the present invention, a Ru complex may preferably be used. Preferably, a Ru complex represented by the chemical formula $[Ru(NH_3)_5X]^{n+}$ may be used. Examples of X in the above formula include $NH_3$, halogen ion, CN, pyridine, nicotinamide and $H_2O$. In the above formula, n+ represents the valence of the oxidative Ru complex, which is determined by the kind of X.

As the oxidoreductase in the present invention, glucose dehydrogenase (GDH) may be used, for example. As the GDH, it is preferable to use PQQGDH, AGDH or CyGDH.

Herein, PQQGDH is GDH whose coenzyme is pyrroloquinoline quinone (PQQ), whereas AGDH and CyGDH indicate those disclosed in International Publication WO02/36779. Specifically, αGDH and CyGDH indicate glucose dehydrogenase (GDH) derived from microorganisms belonging to the *Burkholderia* genus and include those produced by using a transformant.

More specifically, αGDH contains FAD as the prosthetic factor, and a GDH active protein (α subunit) whose molecular weight is about 60 kDa in SDS-polyacrylamide gel electrophoresis under reduced conditions as a subunit having glucose dehydrogenation activity. CyGDH contains, as the subunits, the α subunit and an electron mediator protein (cytochrome C) whose molecular weight in SDS-polyacrylamide gel electrophoresis under reduced conditions is about 43 kDa. The αGDH or CyGDH may be one further containing a subunit other than the α subunit and cytochrome C.

CyGDH can be obtained by refining an enzyme externally secreted by a microorganism belonging to *Burkholderia cepacia* or by refining an enzyme found internally in this microorganism. The αGDH may be obtained by forming a transformant implanted with a gene coding for the expression of αGDH collected from a microorganism belonging to *Burkholderia cepacia*, for example, and refining an enzyme externally secreted from this transformant, or refining an enzyme found internally in this transformant.

As the microorganism belonging to *Burkholderia cepacia*, *Burkholderia cepacia* KS1 strain can be used, for example. This KS1 strain is deposited on Sep. 25, 2000 as microorganism deposit number FERM BP-7306 with the Patent Organism Depositary of the National Institute of Advanced Industrial Science and Technology (Chuo No. 6, 1-1, Higashi 1-chome, Ttsukuba-shi, Ibaraki, Japan 305-8566).

The glucose sensor according to the present invention may be so designed that a capillary force is generated in the flow path.

According to a third aspect of the present invention, there is provided an analytical method comprising the steps of: supplying, in a state in which a sample containing blood cells is moving, electrons taken from an analysis target component contained in the sample to an electron mediator so that electron transfer from the analysis target component to the electron mediator is substantially completed in said state; causing electron transfer between the electron mediator and an electron detection medium in a state in which the movement of the sample is stopped; and performing computation necessary for analyzing the analysis target component based on information obtained through the electron detection medium.

Similarly to the first aspect of the present invention, there electron detection medium may contain a color former or comprise a conductor.

Herein, examples of sample containing blood cells in the present invention include at least whole blood and controlled solution such as diluted whole blood.

BEST MODE FOR CARRYING OUT THE INVENTION

A first through a fourth embodiments of the present invention will be described below with reference to the accompanying drawings.

The first embodiment of the present invention will be described with reference to FIGS. 1-3.

Figure 1:
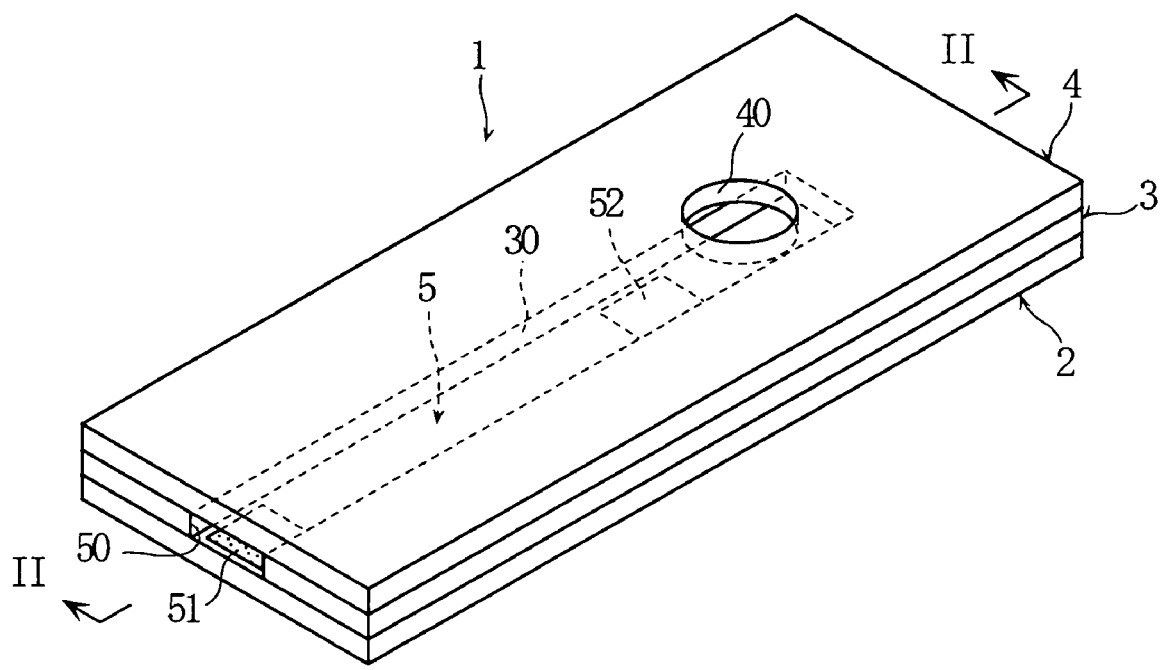
FIG. 1 is an overall perspective view showing a glucose sensor according to a first embodiment of the present invention.
Figure 2:
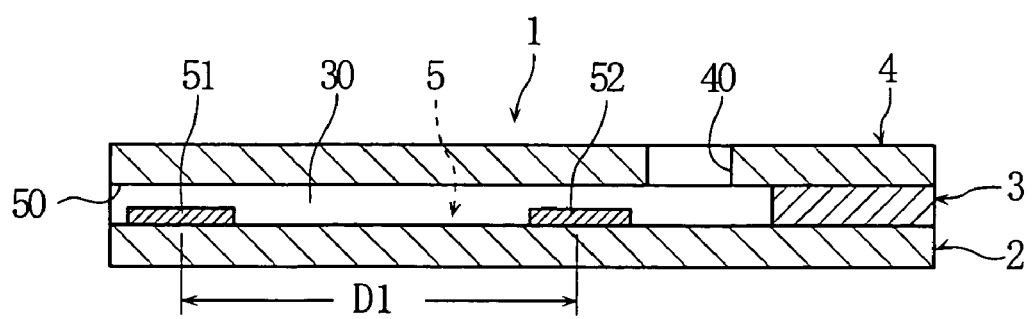
FIG. 2 is a sectional view taken along lines II-II in FIG. 1.
Figure 3:
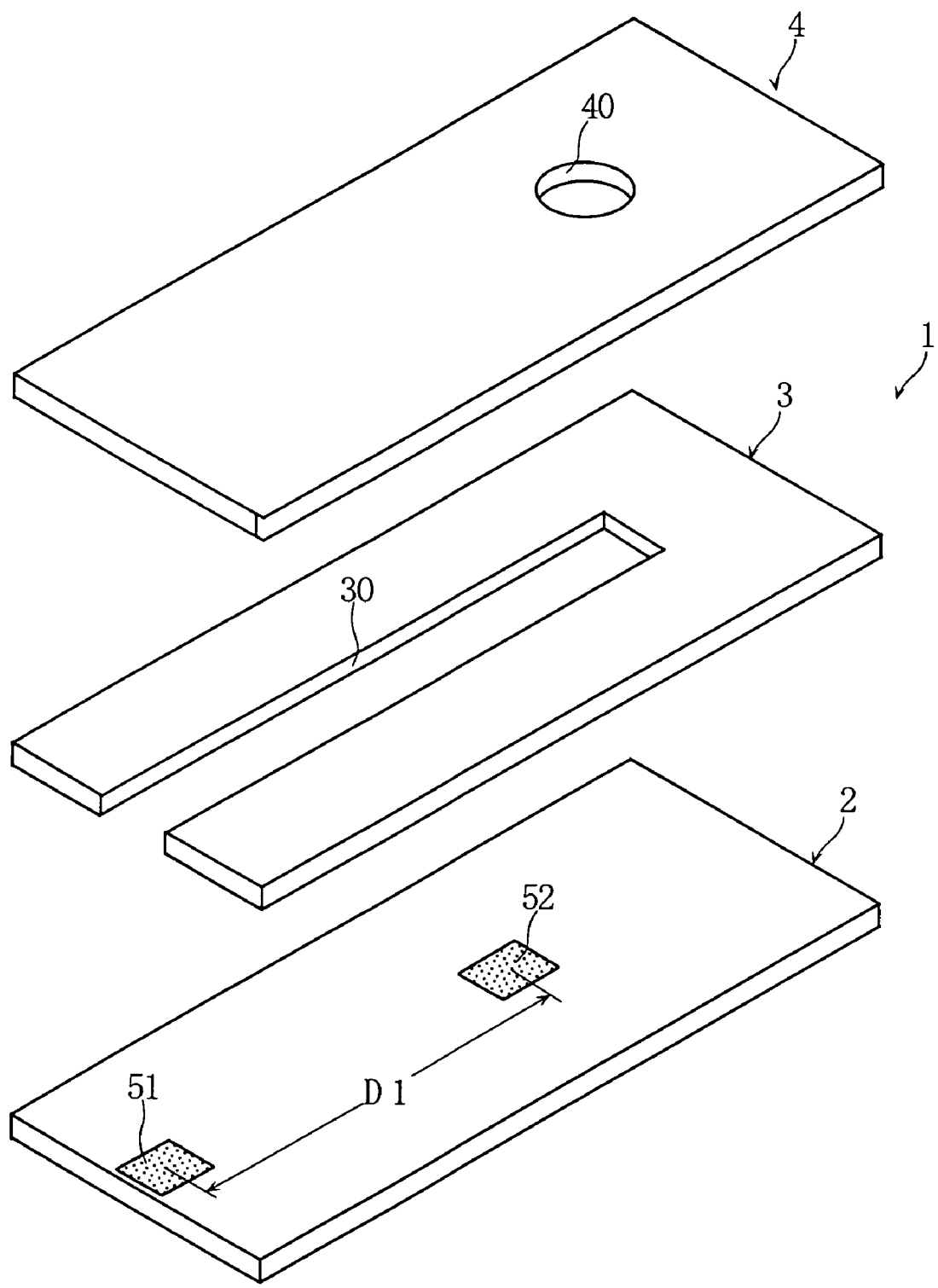
FIG. 3 is an exploded perspective view of the glucose sensor shown in FIG. 1.

The glucose sensor 1 shown in FIGS. 1-3 is a disposable one and designed to measure the glucose level in blood by colorimetry. The glucose sensor 1 includes a substrate 2 having an elongated rectangular shape, and a cover 4 bonded to the substrate via a spacer 3. These elements 2-4 define a capillary 5 extending longitudinally of the substrate 2. The capillary 5 serves to move blood by capillary force and provide a reaction field. The capillary 5 communicates with the outside through an opening 50. The opening 50 is utilized for introducing blood into the capillary 5.

The substrate 2 is made of PET, PMMA or vinylon, for example, to be transparent. The substrate 2 is provided with a first and a second reagent portions 51 and 52 accommodated in the capillary 5.

The first reagent portion 51 is positioned upstream from the second reagent portion 52 in the direction of flow of the blood and adjacent to the opening 50. The first reagent portion contains an oxidoreductase and an electron mediator, for example, and in a solid state soluble in blood. Therefore, when the blood is introduced into the capillary 5, a liquid phase reaction system including glucose, the oxidoreductase, and the electron mediator is established in the capillary 5.

As the oxidoreductase, glucose dehydrogenase (GDH) may be used, for example, and typically, PQQGDH, αGDH or CyGDH may be used.

As the electron mediator, use may be made of a metal complex such as Ru complex or Os complex, for example. Preferably, [Ru(NH$_3$)$_6$]Cl$_3$ is used as the Ru complex. As the electron mediator, PMS (5-methylphenazinium methylsulfate), cytochrome or NAD$^{-1}$ can also be used. The content of the electron mediator is so set that, when the blood contains glucose in the maximum amount of a predetermined measurable concentration range, the electron mediator can receive all the electrons taken from glucose. For instance, when the maximum amount of the measurable range is 600 mg/dL (33 mM) and glucose and the electron mediator react with each other stoichiometrically at the ratio of 1:2, the content of the electron mediator is so set that the concentration when the capillary 5 is filled with blood becomes not lower than 66 mM.

The second reagent portion 52 contains a color former and is in the form of a solid layer which is sparingly soluble in blood. For instance, the second reagent portion 52 has a structure provided by causing gel carrier fixed to the substrate 2 to support a color former. With such an arrangement, the electron mediator can be diffused in the second reagent portion 52 without dispersing the color former into the blood so that electrons from the electron mediator can be supplied to the color former in the second reagent portion 52.

As the gel carrier, use may be made of polyacrylamide or polyvinyl alcohol. Although various kinds of known color former can be used, it is preferable to use a color former whose absorption wavelength in a color-developed state resulting from electron reception differs from the absorption wavelength of blood. For instance, MTT, INT, WST-4 and 4AA can be used as the color former.

Herein, the center-to-center distance D1 between the first reagent portion 51 and the second reagent portion 52 is so set that, when the blood contains glucose in the maximum amount of a predetermined measurable concentration range, the electron transfer from the maximum amount of glucose to the electron mediator can be substantially completed before the blood reaches the second reagent portion 52 (before the electron mediator becomes able to supply electrons to the color former). The center-to-center distance D1 is set appropriately according to the speed at which the oxidoreductase takes electrons from glucose (catalytic power), the speed at which the electron mediator receives electrons from glucose (electron transfer rate) and the moving speed of the blood in the capillary, for example. For instance, when the time required for filling the capillary 5 with blood is two seconds, PQQGDH is used as the oxidoreductase, and $[Ru(NH_3)_6]Cl_3$ is used as the electron mediator, the center-to-center distance D1 is set to the range of 0.5 to 1.0 mm.

The spacer 3 serves to define the distance between the substrate 2 and the cover 4, i.e., the height of the capillary 5. The spacer 3 is formed with a slit 30 which defines the width of the capillary 5.

The cover 4 is entirely transparent. The cover 4 may be made of a material which is similar to that of the substrate 2. The cover 4 is formed with a through-hole 40. The through-hole 40 is provided for discharging gas from the capillary 5 and communicates with the interior of the capillary 5.

Figure 4A:
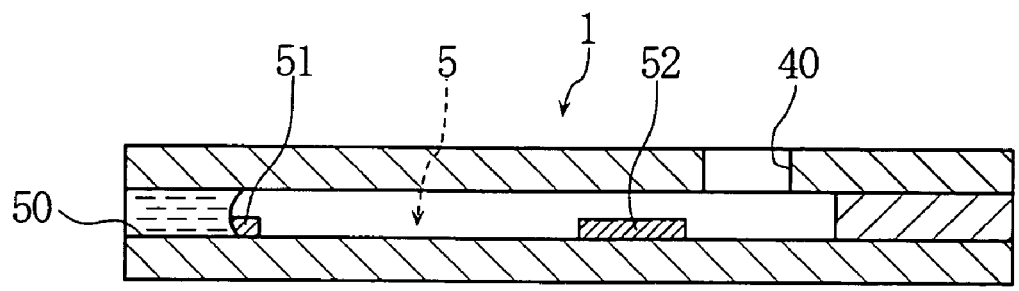
FIG. 4 includes sectional views corresponding to FIG. 2 for describing the operation of the glucose sensor shown in FIG. 1.
Figure 4B:
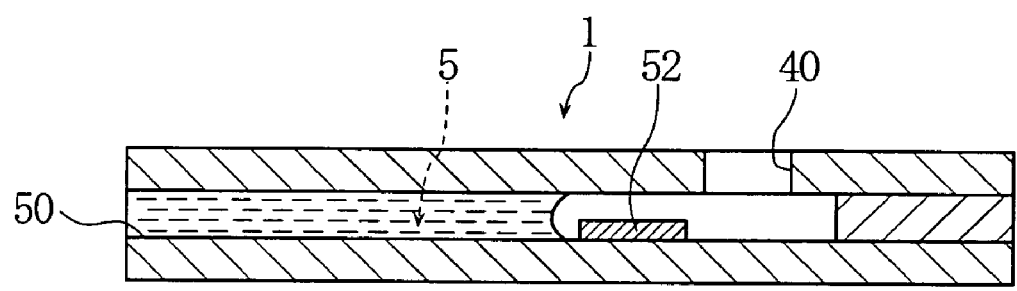
Figure 4C:
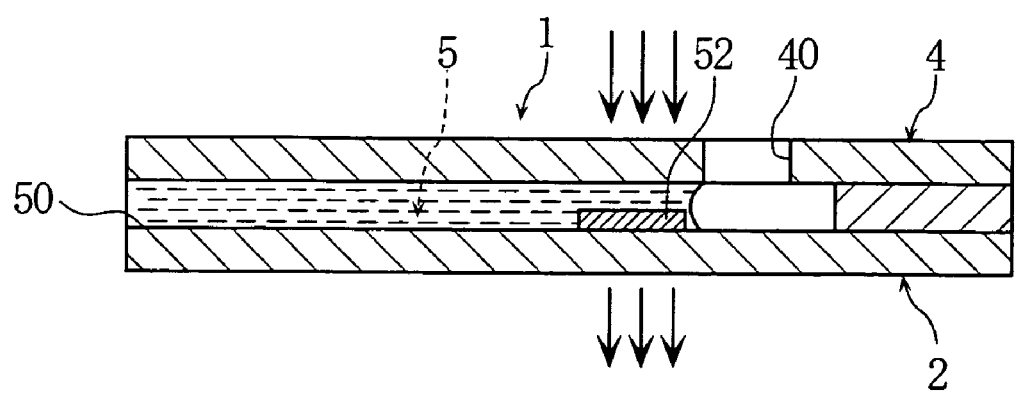

As shown in FIGS. 4A-4C, in the glucose sensor 1, when blood is supplied to the capillary 5 through the opening 50, the blood moves in the capillary 5 by the capillary force generated in the capillary 5. As shown in FIGS. 4A and 4B, as the blood moves, the first reagent portion 51 is dissolved by the blood. Therefore, the oxidoreductase and the electron mediator included in the first reagent portion 51 disperse in the blood and move along with the blood toward the through-hole 40, and hence, to the second reagent portion 52. At this time, the oxidoreductase takes electrons from the glucose in blood serum (blood plasma) to convert glucose to gluconolactone, whereby the glucose level in blood serum (blood plasma) drops. The electrons taken from the glucose are supplied to the electron mediator by the action of the oxidoreductase. As the glucose level in the blood serum (blood plasma) drops, glucose in blood cells moves into the blood serum (blood plasma). Similarly to the above, electrons are taken from the glucose moved out of the blood cells and supplied to the electron mediator.

As shown in FIG. 4C, the movement of the blood stops when the blood reaches the through-hole 40. At this time, the blood permeates into the second reagent portion 52. Since the electron mediator moves together with the blood through the capillary 5, the electron mediator diffuses into the second reagent portion 52 in accordance with the permeation of the blood into the second reagent portion 52. Therefore, in the second reagent portion 52, electrons are supplied from the electron mediator to the color former to cause the color former to develop a color, whereby the second reagent portion 52 is colored. After a predetermined time period has elapsed from the start of the blood supply, the degree of coloring of the second reagent portion 52 is grasped by irradiating the second reagent portion 52 with light via the cover 4 and receiving the light passed through or reflected at the second reagent portion 52 and the substrate 2, for example. As the light to irradiate the liquid phase reaction system, use is made of light having a wavelength which is well absorbed by the developed color of the color former. For instance, the glucose level can be computed based on the ratio between the intensity of the incident light and the intensity of the transmitted light.

In the glucose sensor 1, the first reagent portion 51 is arranged upstream from the second reagent portion 52 in the blood flow direction. Therefore, it is possible to cause the electron mediator to react with glucose at the same time as the introduction of blood into the capillary 5. Further, since the first reagent portion 51 is positioned close to the opening 50, relatively long time can be ensured for the reaction of the electron mediator with glucose before the blood reaches the second reagent portion 52. As a result, the electron mediator can actively react with glucose before the electron mediator reaches the second reagent portion 52 (before the electron mediator reacts with the color former). Particularly, in the glucose sensor 1, the content of the electron mediator is so set that the electron mediator can receive all the electrons taken from glucose of the maximum amount of a predetermined measurable concentration range. Further, the center-to-center distance D1 is so set that the electron transfer from all of the glucose to the electron mediator is substantially completed before the blood reaches the second reagent portion 52. Therefore, in the glucose sensor 1, the glucose in the blood cells can reliably move to the blood serum (blood plasma) before the electron mediator starts to react with the color former. As a result, the influence of the blood cell concentration in blood can be suppressed, so that the glucose level can be measured accurately.

Figure 5:
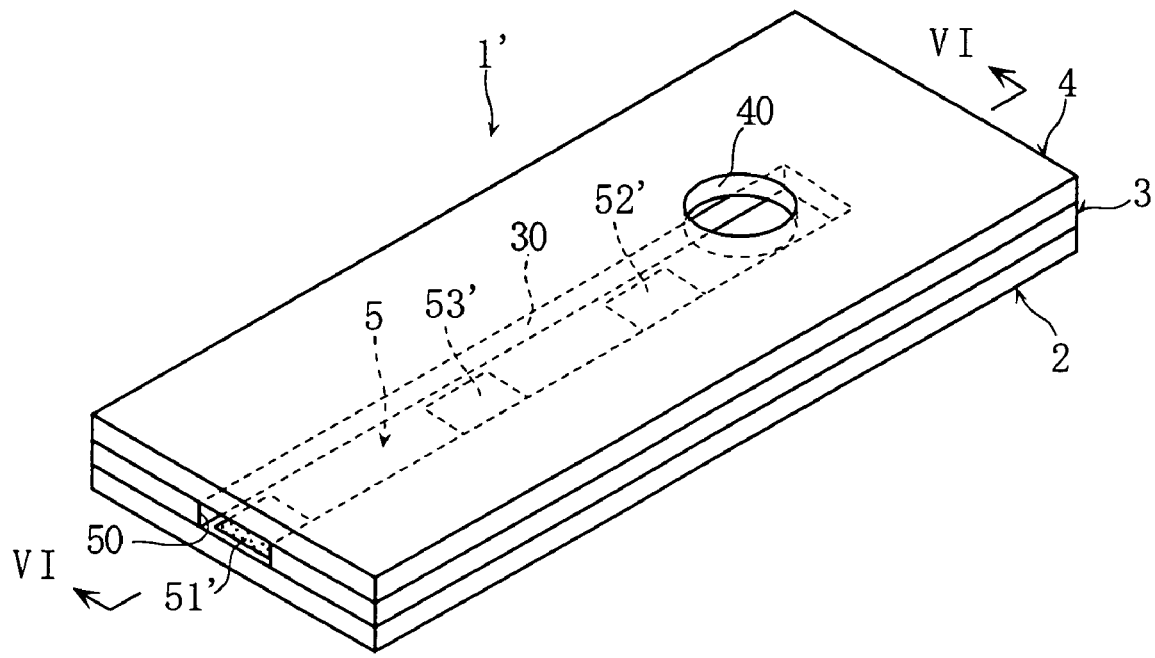
FIG. 5 is an overall perspective view showing a glucose sensor according to a second embodiment of the present invention.
Figure 6:
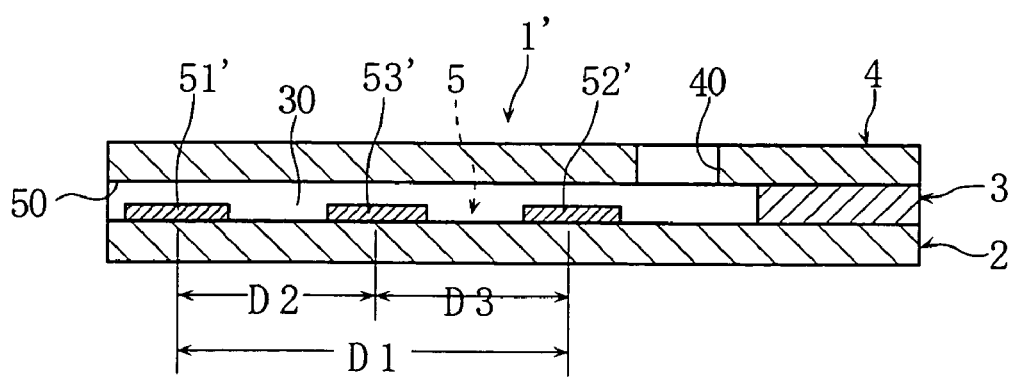
FIG. 6 is a sectional view taken along lines VI-VI in FIG. 5.
Figure 7:
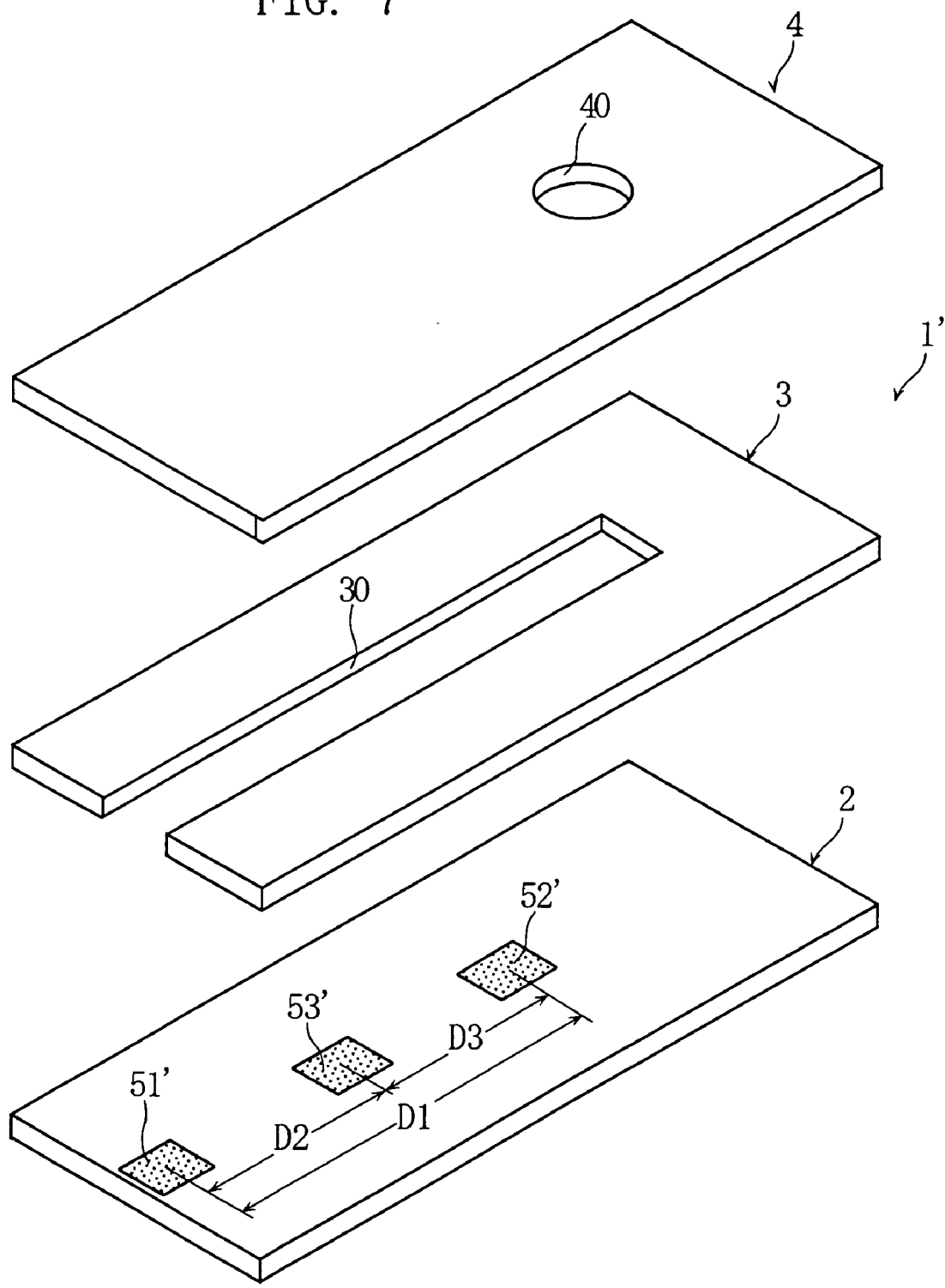
FIG. 7 is an exploded perspective view of the glucose sensor shown in FIG. 5.

A glucose sensor according to the second embodiment of the present invention will be described below with reference to FIGS. 5-7. In FIGS. 5-7, the elements which are identical or similar to those of the foregoing glucose sensor 1 (See FIGS. 1-3) are designated by the same reference signs as those used for the foregoing glucose sensor, and overlapping description thereof is omitted.

The glucose sensor 1' shown in FIGS. 5-7 differs from the foregoing glucose sensor 1 (See FIGS. 1-3) in that the glucose sensor 1' includes a first through a third reagent portions 51', 52' and 53'.

The first reagent portion 51' contains an electron mediator and dissolves when a sample is supplied to the capillary 5. The first reagent portion 51' is arranged adjacent to an opening 50. As the electron mediator to be contained in the first reagent portion 51', an electron mediator similar to that of the foregoing glucose sensor 1 (See FIGS. 1-3) may be used.

The second reagent portion 52' has a structure which is similar to that of the second reagent portion 52 of the foregoing glucose sensor 1 (See FIGS. 1-3). Specifically, for example, the second reagent portion 52' has a structure provided by causing gel carrier, which is sparingly soluble in blood, to support a color former as the electron detection medium.

The third reagent portion 53' contains an oxidoreductase and dissolves when the sample is supplied to the capillary 5. The third reagent portion 53' is provided between the first reagent portion 51' and the second reagent portion 52'. Examples of oxidoreductase to be contained in the third reagent portion 53' are similar to those of the foregoing glucose sensor 1 (See FIGS. 1-3).

The center-to-center distance D1 between the first reagent portion 51' and the second reagent portion 52' is set similarly to that of the glucose sensor 1 (See FIGS. 1-3). Specifically, the center-to-center distance D1 is so set that, when the blood contains glucose in the maximum amount of the predetermined measurable concentration range, the electron transfer from the maximum amount of glucose to the electron mediator is substantially completed before the blood reaches the second reagent portion 52' (before the electron mediator becomes able to supply electrons to the color former). On the other hand, the center-to-center distance D2 between the first reagent portion 51' and the third reagent portion 53' is so set that almost the maximum amount of glucose which can be taken out from the blood cells due to the existence of the electron mediator in the first reagent portion can be taken out. The center-to-center distance D3 between the second reagent portion 52' and the third reagent portion 53' is so set that the third reagent portion 53' dissolves sufficiently and the oxidoreductase disperses sufficiently in the blood.

In the glucose sensor 1', when blood is supplied to the capillary 5, the first reagent portion 51' first dissolves to disperse the electron mediator in the blood. At this time, the existence of the electron mediator, which is an inorganic material, around the blood cells promotes the diffusion of glucose from the inside to the outside of the blood cells. Subsequently, when the blood reaches the third reagent portion 53', the third reagent portion 53' dissolves to disperse oxidoreductase in the blood. By the action of the oxidoreductase, the reaction between the glucose in the blood serum and the electron mediator is promoted. When the blood finally reaches the second reagent portion 52', electrons are supplied from the electron mediator to the color former by the action of the oxidoreductase, whereby the color former develops a color.

In the glucose sensor 1', the glucose in blood cells is positively taken out before the glucose in the blood serum is supplied to the electron mediator. That is, the glucose level in the blood serum is increased before the oxidoreductase is caused to act on the electron mediator so that the diffusion of glucose from the blood cells after the oxidoreductase is caused to act on the electron mediator is suppressed. As a result, as will be clear from the Examples described later, the initial reaction speed between the electron mediator and the color former increases, so that the measurement time can be shortened.

Figure 8:
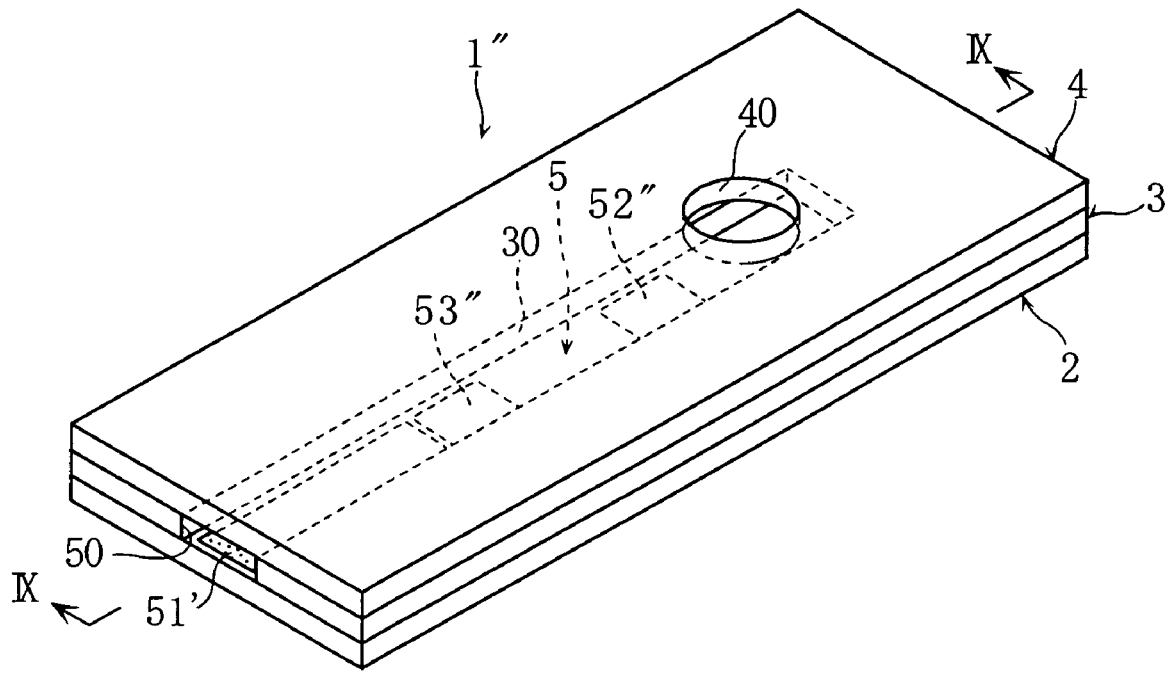
FIG. 8 is an overall perspective view showing a glucose sensor according to a third embodiment of the present invention.
Figure 9:
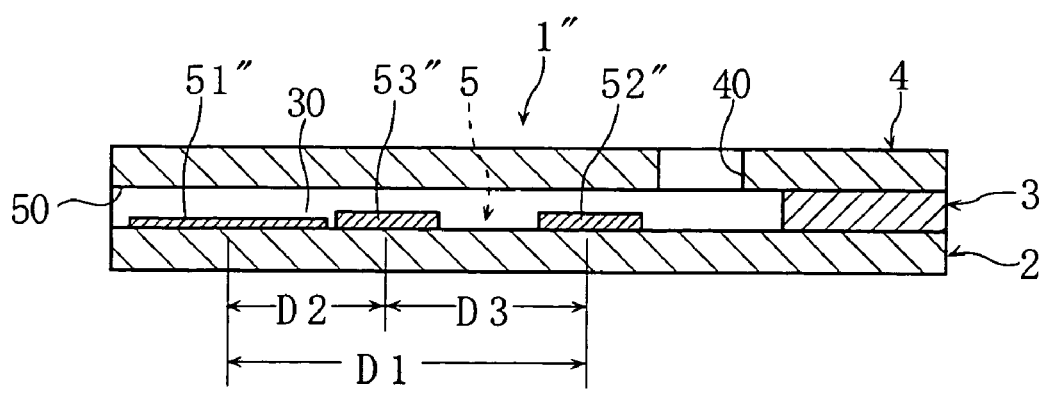
FIG. 9 is a sectional view taken along lines IX-IX in FIG. 8.
Figure 10:
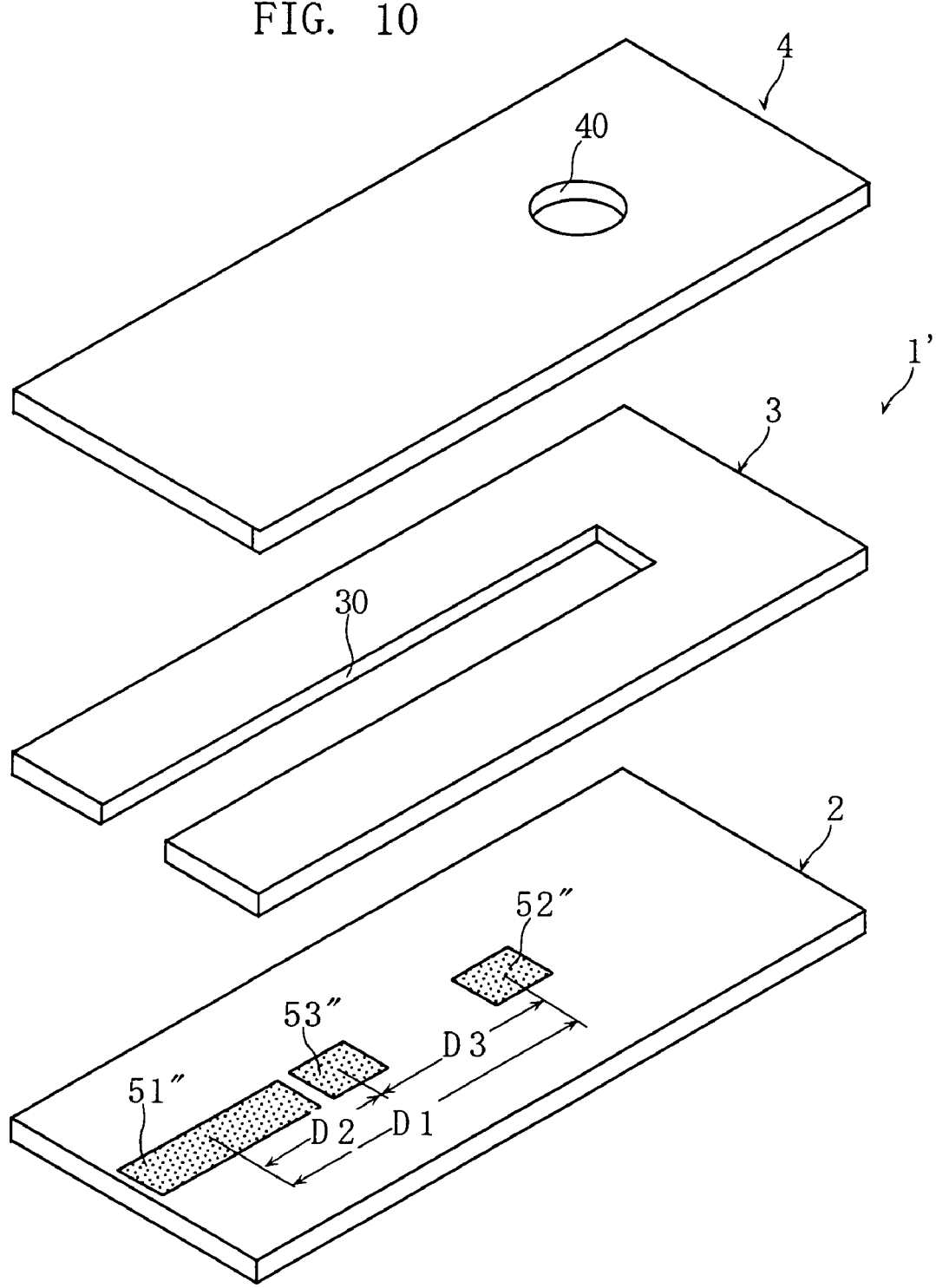
FIG. 10 is an exploded perspective view of the glucose sensor shown in FIG. 8.

A glucose sensor according to the third embodiment of the present invention will be described below with reference to FIGS. 8-10. In FIGS. 8-10, the elements which are identical or similar to those of the foregoing glucose sensors 1, 1' (See FIGS. 1-3 or FIGS. 5-7) are designated by the same reference signs as those used for the foregoing glucose sensors, and overlapping description thereof is omitted.

The glucose sensor 1" shown in FIGS. 8-10 includes a first through a third reagent portions 51", 52" and 53", which differs from the glucose sensor 1 (See FIGS. 1-3) of the first embodiment but is similar to the glucose sensor 1' of the second embodiment (See FIGS. 5-7). The structure of the first reagent portion 51" of the glucose sensor 1" differs from that of the glucose sensor 1' (See FIGS. 5-7) of the second embodiment.

The first reagent portion 51" contains an electron mediator similar to that of the foregoing glucose sensors 1 and 1' and dissolves when a sample is supplied to the capillary 5. The first reagent portion 51" spreads between the opening 50 and the third reagent portion 53".

The first reagent portion 51" has an elongated rectangular shape and is larger than the second reagent portion 52" and the third reagent portion 53" in area as viewed in plan and length in the blood flow direction in the capillary 5. Specifically, the first reagent portion 51" has a length which accounts for 50 to 90% of the distance from the opening 50 to the edge of the third reagent portion 53" on the opening 50 side, and a thickness which is 15 to 80% of that of the third reagent portion 53", for example. This numerical range is set in view of the limit of manufacturing and so that the solubility of the first reagent portion 51" can be sufficiently improved. The area in plan view of the first reagent portion 51" is 1.5 to 10 times that of the second reagent portion 53".

The center-to-center distance D1 between the first reagent portion 51" and the second reagent portion 52" is so set that, when the blood contains glucose in the maximum amount of the predetermined measurable concentration range, the electron transfer from the maximum amount of glucose to the electron mediator is substantially completed before the blood reaches the second reagent portion 52" (before the electron mediator becomes able to supply electrons to the color former). On the other hand, the center-to-center distance D2 between the first reagent portion 51" and the third reagent portion 53" is so set that almost the maximum amount of glucose which can be taken out from the blood cells due to the existence of the electron mediator in the first reagent portion can be taken out. The center-to-center distance D3 between the second reagent portion 52" and the third reagent portion 53" is so set that the third reagent portion 53' dissolves sufficiently and that the oxidoreductase can be dispersed sufficiently in the blood.

In the glucose sensor 1", the first reagent portion 51" is thinly spread. Therefore, when blood is supplied to the capillary 5, the solubility of the first reagent portion 51" is high, and the electron mediator readily disperses in the blood. Therefore, in the mixed system of the blood and the electron mediator which is established when the blood is supplied to the capillary 5, the variation in the concentration of the electron mediator is small. As a result, the variation in the reaction speed is suppressed, so that the reproducibility of measurements is improved in a low concentration range in which measurements are likely to be influenced by the variation in the concentration of the electron mediator. Moreover, in the glucose sensor 1", similarly to the glucose sensor 1', the glucose in blood cells is positively taken out before the glucose in the blood serum is supplied to the electron mediator. Therefore, the initial reaction speed between the electron mediator and the color former increases, so that the measurement time can be shortened.

A glucose sensor according to the fourth embodiment of the present invention will be described below with reference to FIGS. 11-13.

Figure 11:
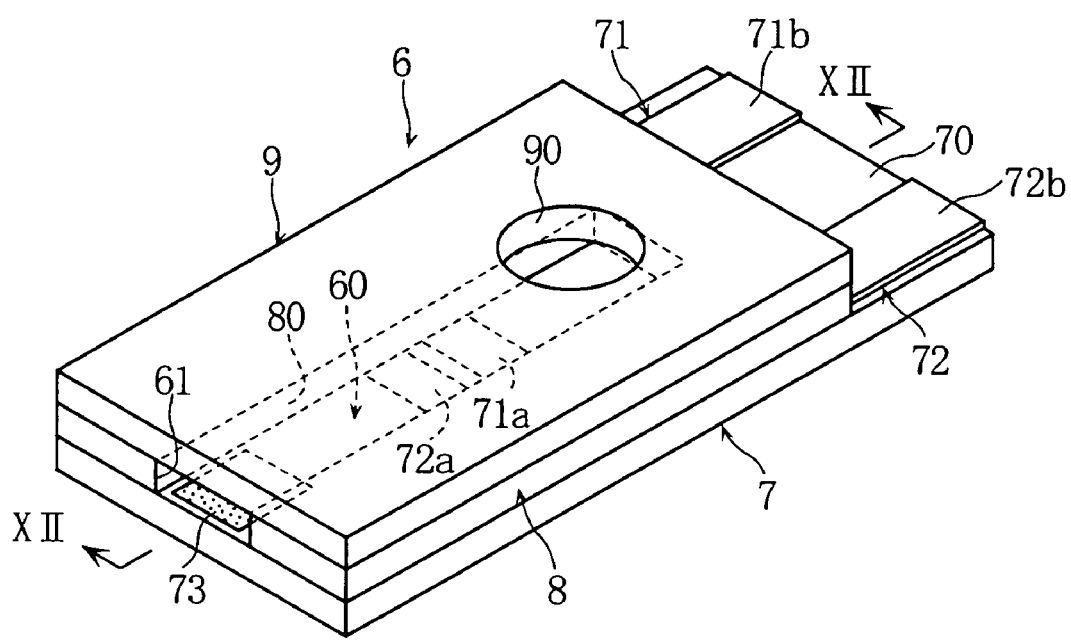
FIG. 11 is an overall perspective view showing a glucose sensor according to a fourth embodiment of the present invention.
Figure 12:
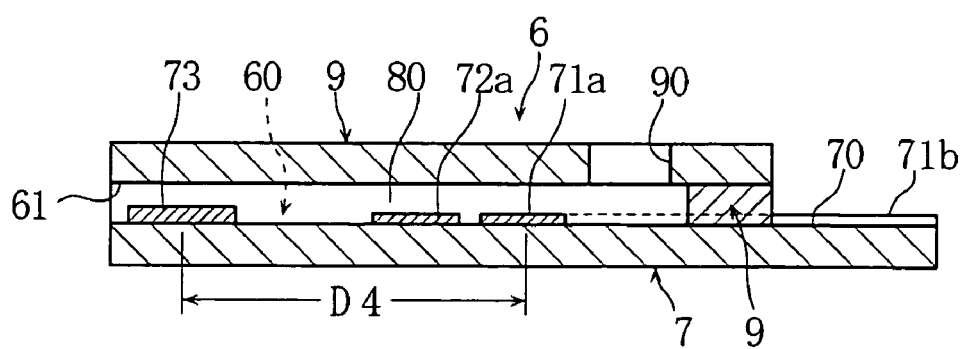
FIG. 12 is a sectional view taken along lines XII-XI in FIG. 11.
Figure 13:
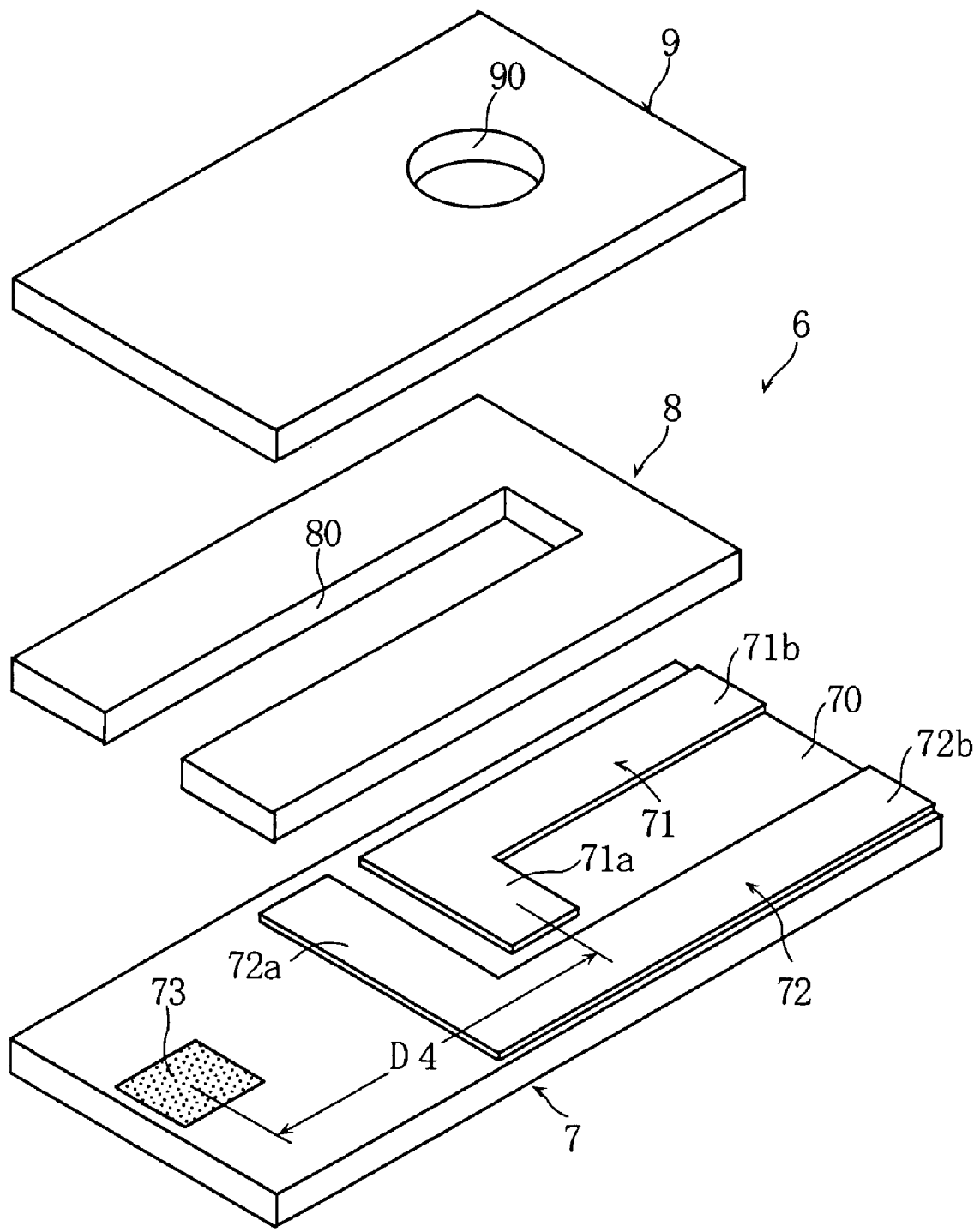
FIG. 13 is an exploded perspective view of the glucose sensor shown in FIG. 11.

The glucose sensor shown in FIGS. 11-13 is a disposable one and designed to measure the glucose level in blood by an electrode method. Similarly to the foregoing glucose sensor 1 (See FIGS. 1-3), the glucose sensor 6 includes a substrate 7, and a cover 9 bonded to the substrate via a spacer 8. The elements 7-9 define a capillary 60.

The structures of the spacer 8 and the cover 9 are similar to those of the spacer 3 and the cover 4 (See FIGS. 1-3) of the foregoing glucose sensor 1. Specifically, the spacer 8 is formed with a slit 80 defining the width of the capillary 60, and the cover 9 is formed with a through-hole 90 communicating with the interior of the capillary 60. The cover 9 need not necessarily be transparent.

The substrate 7 has an upper surface 70 provided with a working electrode 71, a counter electrode 72 and a reagent portion 73. The working electrode 71 and the counter electrode 72 have respective first ends 71a and 72a extending in the width direction of the substrate 7. The first ends 71a and 72a are arranged at locations relatively close to the through-hole 90 to be spaced from each other in the longitudinal direction of the substrate 7 and partially face the interior of the capillary 60. The working electrode 71 and the counter electrode 72 have respective second ends 71b and 72b which are exposed on the outside of the capillary 60. The second ends 71b and 72b are the portions to be brought into contact with the terminals such as probes, for example, in producing a potential difference between the first ends 71a and 72a.

The reagent portion 73 is provided in the capillary 60 and adjacent to an opening 61. The reagent portion 73 is spaced from the first ends 71a and 72a of the working electrode 71 and the counter electrode 72 and positioned upstream in the direction of flow of a sample in the capillary 60. The reagent portion 73 is in a solid state containing an oxidoreductase and an electron mediator, for example. The reagent portion 73 is designed to easily dissolve in blood. As the oxidoreductase and the electron mediator, an oxidoreductase and an electron mediator similar to those of the first reagent portion 51 (See FIGS. 1-3) of the glucose sensor 1 may be used.

The content of the electron mediator in the reagent portion 73 is so set that, when the blood contains glucose in the maximum amount of a predetermined measurable concentration range, the electron mediator can receive all the electrons taken out from the maximum amount of glucose. Further, the center-to-center distance D4 between the reagent portion 73 and the end 71a of the working electrode 71 is so set that, when the blood contains glucose in the maximum amount of the predetermined measurable concentration range, the electron transfer from the maximum amount of glucose to the electron mediator is substantially completed before the blood reaches the end 71a of the working electrode 71.

In the glucose sensor 6 again, when blood is supplied to the capillary 60 through the opening 61, the blood moves in the capillary 60 by the capillary force generated in the capillary 60. As the blood moves, the reagent portion 73 is dissolved by the blood. At this time, electrons are taken from the glucose in the blood serum (blood plasma) by the oxidoreductase, and the electrons taken from the glucose are supplied to the electron mediator by the action of the oxidoreductase. As the glucose in the blood is consumed, the glucose in blood cells moves into the blood serum (blood plasma). In a manner similar to the above, electrons are taken out from the glucose moved out of the blood cells and supplied to the electron mediator. The movement of the blood stops when the blood reaches the through-hole 90. At this time, the electron mediator exists on the surface of the end 71a of the working electrode 71. By applying a voltage between the working electrode 71 and the counter electrode 72, electrons are supplied from the electron mediator to the end 71a of the working electrode 71. The glucose level is computed based on the amount of electrons supplied from the electron mediator to the end 71a of the working electrode 71.

In the glucose sensor 6, the reagent portion 73 is arranged upstream from the end 71a of the working electrode 71 in the direction of the flow of the blood and also adjacent to the opening 50. Therefore, the electron mediator can positively react with glucose before it reaches the end 71a of the working electrode 71. Therefore, in the glucose sensor 6, similarly to the foregoing glucose sensor 1 (See FIGS. 1-3), the influence of the concentration of blood cells in the whole blood can be suppressed, so that the glucose level can be measured accurately.

In the glucose sensor 6, the reagent portion 73 contains an electron mediator and an oxidoreductase. However, similarly to the foregoing glucose sensors 1' and 1" (See FIGS. 8-10 and 11-13), reagent portions respectively containing an electron mediator and an oxidoreductase may be provided separately.

The present invention is also applicable to a glucose sensor designed to use a sample other than blood, such as diluted blood. Further, the present invention is also applicable to an analytical tool designed to analyze a component other than glucose, such as cholesterol or lactic acid.

Example 1

In this example, in the measurement of a blood glucose level using a glucose sensor for colorimetry, the influence of the blood cell concentration (hematocrit(Hct)) in blood on the measurement result was examined. As the glucose sensor, sensors (1)-(3) having the structures described below were used. The influence of an Hct on the measurement result was examined based on the time course of absorbance and the bias after the lapse of a predetermined time period.

(Basic Structure of Glucose Sensor)

Figure 14:
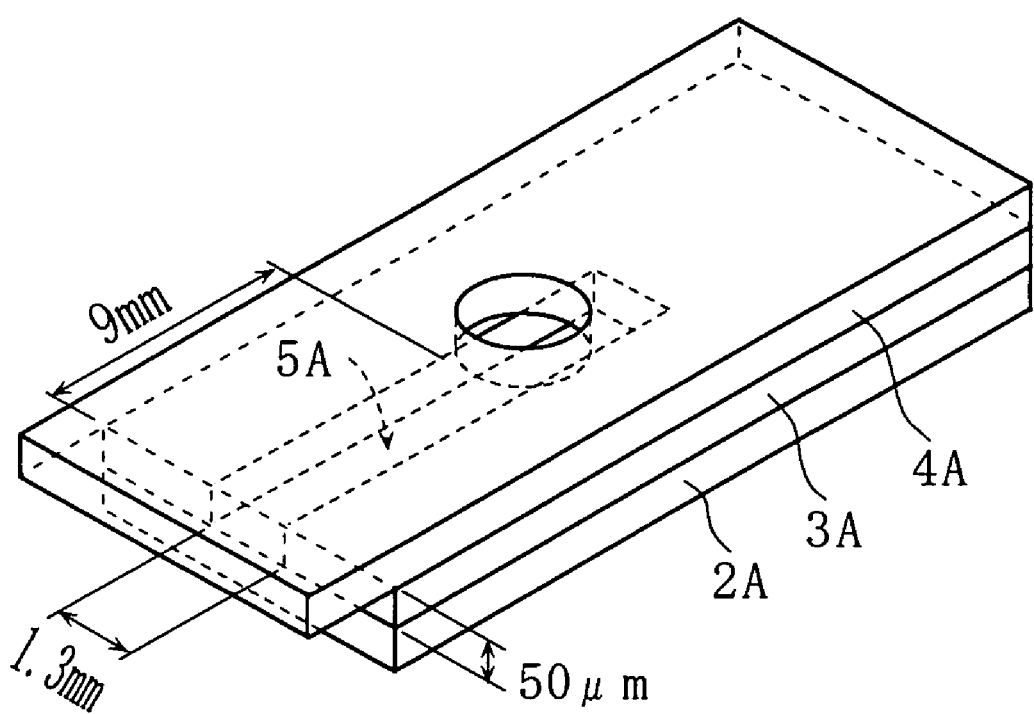
FIG. 14 is a perspective view for describing the basic structure of the glucose sensors used in Examples 1-3.

The basic structure of the glucose sensors (1)-(3) (excluding reagent portions) is shown in FIG. 14. Specifically, each of the glucose sensors (1)-(3) included a transparent substrate 2A, a transparent cover 4A bonded to the substrate via a spacer 3A, and a capillary 5A defined by the elements 2A-4A. As described in FIG. 14, the dimensions of the capillary 5A were 1.3 mm×9 mm×50 μm. The transparent substrate 2A and the transparent cover 4A were made of a PET material having a thickness of 250 μm. The spacer 3A was prepared by using a double-sided tape.

(Structure and Preparation of Reagent Portions)

In each of the glucose sensors (1)-(3), a reagent portion containing a color former was provided to be spaced from a reagent portion containing at least either one of an electron mediator and an oxidoreductase in the flow direction in the capillary.

Figure 15A:
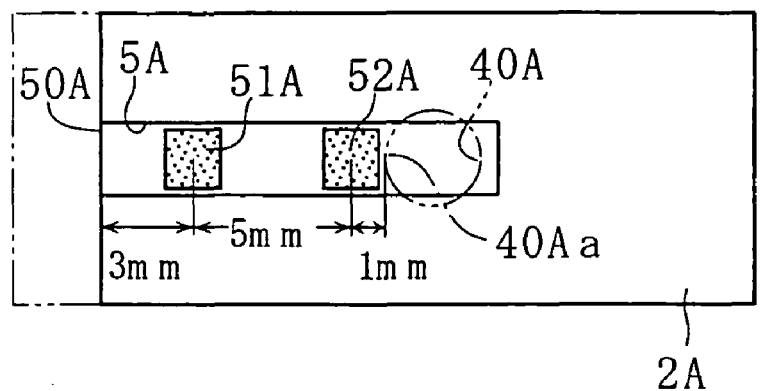
FIG. 15 includes plan views for describing the structure of reagent portions of the glucose sensors used in Examples 1-3, in which the transparent cover is omitted.

Specifically, as shown in FIG. 15A, the glucose sensor (1) (inventive glucose sensor) included a first reagent portion 51A containing an electron mediator and an oxidoreductase and provided on the upstream side in the capillary 5A, and a second reagent portion 52A containing a color former and provided on the downstream side in the capillary. Specifically, the first reagent portion 51A was so formed that the center thereof was positioned 3 mm away from the sample introduction port 50A and so as to dissolve in blood. The second reagent portion 52A was so formed that the center thereof was positioned 1 mm away from the most upstream point 40Aa of the through-hole 40A and fixed to the transparent substrate 2A. The second reagent portion was prepared by causing a gel carrier, which was fixed to the transparent substrate 2A and sparingly soluble in blood, to support a color former. The center-to-center distance between the first reagent portion 51A and the second reagent portion 52A was set to 5 mm.

Each of the first and the second reagent portions 51A and 52A was formed by applying the liquid material to the intended portion and then drying the liquid material by blowing (30 C.°, 10% Rh). The composition and the application amount of the liquid material to form the first and the second reagent portions 51A and 52A are respectively given in Table 1 and Table 2 below.

TABLE 1

|  | PQQGDH | [Ru(NH$_3$)$_6$]Cl$_3$ | CHAPS | Sucrose monolaurate | ACES (pH 7.5) | Application Amount |
|---|---|---|---|---|---|---|
| First Reagent Portion | 7.5 kU/mL | 200 mM | 0.20% | 0.05% | 75 mM | 0.2 µL |

TABLE 2

|  | MTT | Polyacrylamide | Methanol | Application Amount |
|---|---|---|---|---|
| Second Reagent Portion | 60 mM | 0.40% | 50% | 0.2 µL |

Figure 15B:
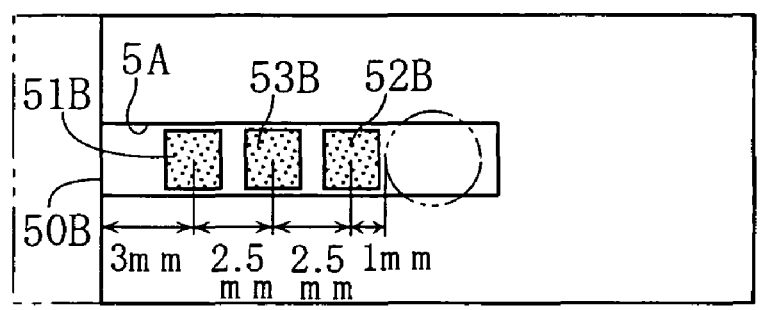

As shown in FIG. 15B, the glucose sensor (2) (inventive glucose sensor) included a first reagent portion 51B which was provided similarly to that of the glucose sensor (1) (See FIG. 15A) but did not contain an oxidoreductase. The glucose sensor (2) included a third reagent portion 53B containing an oxidoreductase and arranged between the first reagent portion 51B and the second reagent portion 52B. The third reagent portion 53B was so arranged that the center thereof is located at the intermediate position between the center of the first reagent portion 51B and the center of the second reagent portion 52B.

Each of the first through the third reagent portions 51B, 52B and 53B was formed by applying the liquid material to the intended portion and then drying the liquid material by blowing (30 C.°, 10% Rh). The composition and the application amount of the liquid material to form the first, the second and the third reagent portions 51B, 52B and 53B are respectively given in Table 3, Table 4 and Table 5 below.

TABLE 3

|  | [Ru(NH$_3$)$_6$]Cl$_3$ | Application Amount |
|---|---|---|
| First Reagent Portion | 200 mM | 0.2 µL |

TABLE 4

|  | MTT | Polyacrylamide | Methanol | Application Amount |
|---|---|---|---|---|
| Second Reagent Portion | 60 mM | 0.40% | 50% | 0.2 µL |

TABLE 5

|  | PQQGDH | CHAPS | Sucrose monolaurate | ACES (pH 7.5) | Application Amount |
|---|---|---|---|---|---|
| Third Reagent Portion | 15 kU/mL | 0.20% | 0.05% | 75 mM | 0.1 µL |

Figure 15C:
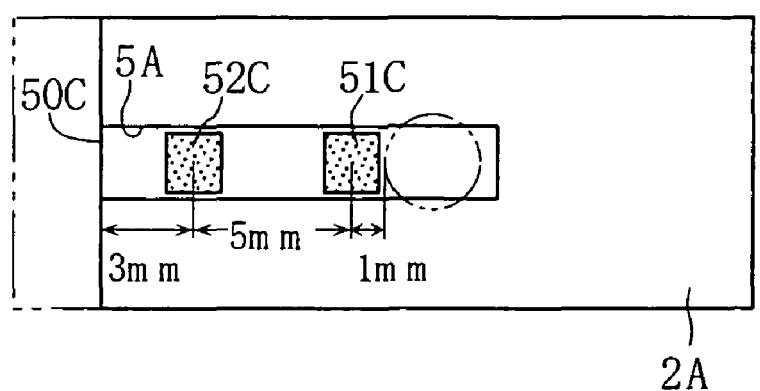

As shown in FIG. 15C, the glucose sensor (3) (comparative glucose sensor) had a structure obtained by changing the position of the reagent portion containing a color former and that of the reagent portion containing an electron mediator and an oxidoreductase of the glucose sensor (1) (See FIG. 15). Specifically, the first reagent portion 51C was provided at a location corresponding to the second reagent portion 52A of the glucose sensor (1) (i.e., on the downstream side). The first reagent portion 51C was fixed to the transparent substrate 2A, with an electron mediator and an oxidoreductase supported by gel carrier sparingly soluble in blood. The second reagent portion 52C was provided at a location corresponding to the first reagent portion 51A of the glucose sensor (1) (i.e., on the upstream side) to be soluble in blood.

Each of the first and the second reagent portions 51C and 52C was formed by applying the liquid material to the intended portion and then drying the liquid material by blowing (30 C.°, 10% Rh). The composition and the application amount of the liquid material to form the first and the second reagent portions 51C and 52C are respectively given in Table 6 and Table 7 below.

TABLE 6

|  | PQQGDH | [Ru(NH$_3$)$_6$]Cl$_3$ | CHAPS | Sucrose monolaurate | polyacrylamide | ACES (pH 7.5) | Application Amount |
|---|---|---|---|---|---|---|---|
| First Reagent Portion | 30 kU/mL | 200 mM | 0.02% | 0.05% | 0.40% | 75 mM | 0.2 µL |

TABLE 7

|  | MTT | Methanol | Application Amount |
|---|---|---|---|
| Second Reagent Portion | 60 mM | 50% | 0.2 μL |

In Tables 1-7, CHAPS is an abbreviation of 3-[(3-cholamidopropyl)dimethylammonio]propanesulfonic acid, ACES is an abbreviation of N-(2-acetamido)-2-aminoethanesulfonic acid, and MTT is an abbreviation of 3-(4,5-Dimethyl-2-thiazolyl)-2,5-diphenyl-2H-tetrazolium bromide. As the CHAPS, use was made of "KC062" available from DOJINDO LABORATORIES (Japan). As the ACES, use was made of "ED067" available from DOJINDO LABORATORIES (Japan). As the MTT, use was made of "M009" available from DOJINDO LABORATORIES (Japan). As the PQQGDH, use was made of one available from DOJINDO LABORATORIES (Japan). As the $[Ru(NH_3)_6]Cl_3$, use was made of "LM722" available from DOJINDO LABORATORIES (Japan). As the sucrose monolaurate, use was made of "PV689" available from DOJINDO LABORATORIES (Japan). As the polyacrylamide, use was made of "Z2T8071" available from NACALAI TESQUE, INC (Japan).

(Measurement of Time Course of Absorbance)

The time course of absorbance was obtained by repetitively measuring the absorbance with intervals of 0.1 seconds after the analyte was supplied to the capillary. The absorbance was measured by illuminate the second reagent portion 52A, 52B in the case of the glucose sensors (1), (2) and the first reagent portion 51C in the case of the glucose sensor (3) with light traveling in the height direction of the capillary and receiving the light transmitted through each of the glucose sensors (1)-(3). In the illumination, the light having a wavelength 630 nm was directed using a light emitting diode. The transmitted light was received by a photodiode. The absorbance was computed by the formula as follows:

$$Absorbance = \log(I_0/I)$$

(where $I_0$ is the intensity of the incident light, and I is the intensity of the transmitted light)

Figure 16A:
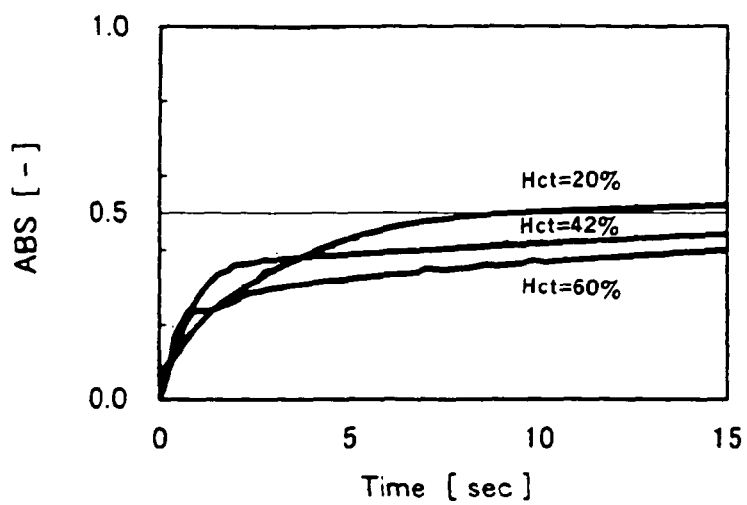
FIG. 16A is a graph showing the time course of absorbance measured using the glucose sensor (1) in Example 1.
Figure 16B:
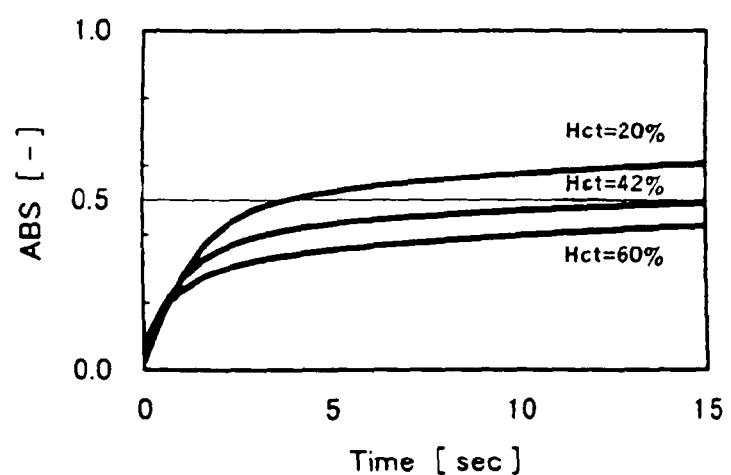
FIG. 16B is a graph showing the time course of absorbance measured using the glucose sensor (2) in Example 1.
Figure 16C:
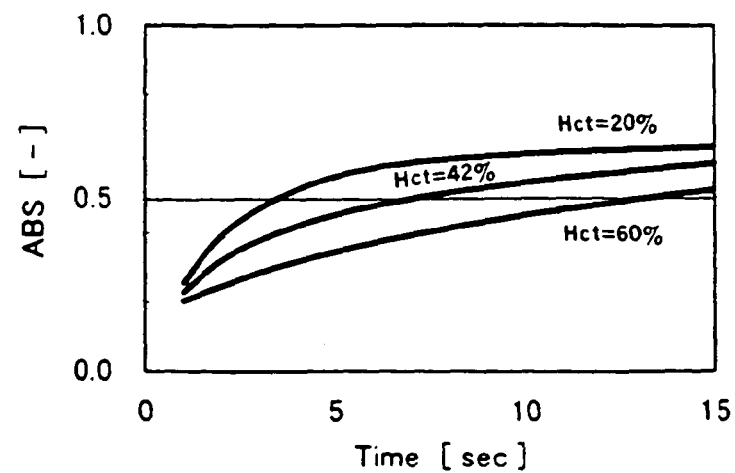
FIG. 16C is a graph showing the time course of absorbance measured using the glucose sensor (3) in Example 1.
Figure 17:
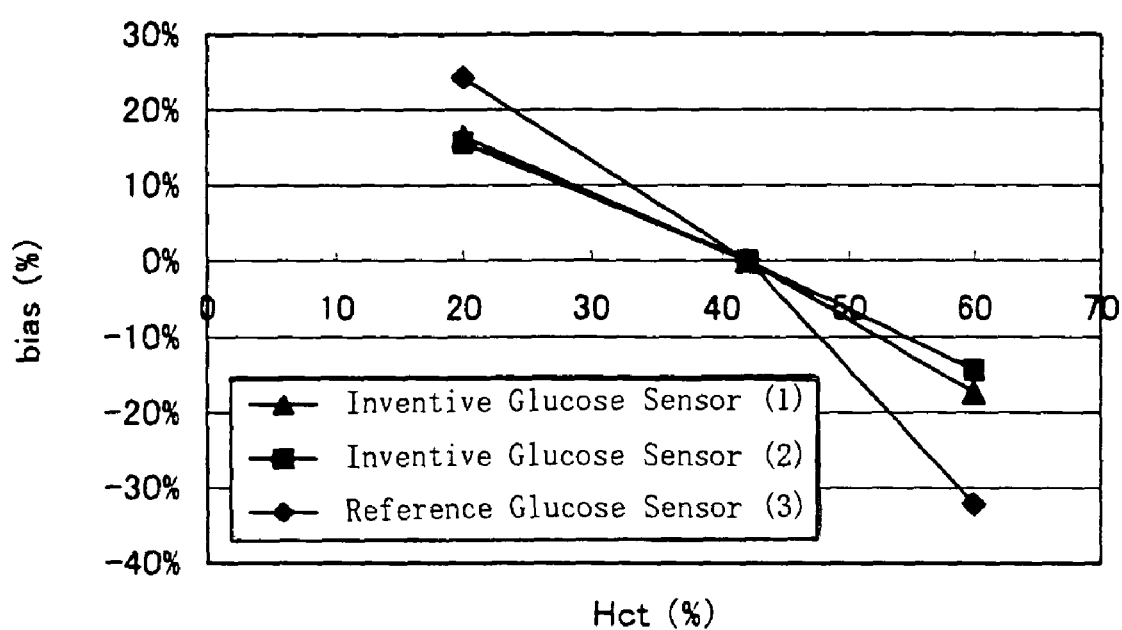
FIG. 17 is a graph showing the influence of Hct in terms of the bias with respect to 42% Hct as the reference.

The time course of absorbance of each of the glucose sensors (1)-(3) was measured five times with respect to each of three kinds of analytes having different hematocrit levels (Hct=20%, 42%, 60%). The glucose level of the analytes was controlled to 430 mg/dL. FIGS. 16A, 16B and 16C show the time courses of absorbance of the glucose sensors (1), (2) and (3), respectively. FIG. 17 shows the computation results of the bias. Specifically, the bias was computed based on the absorbances five seconds after the start of the measurement and is shown in FIG. 17 as the average of five times of measurements with respect to each of the glucose sensors (1)-(3) and each of the Hct levels of the analytes.

As will be understood from FIGS. 16A-16C, in the glucose sensors (1), (2) (inventive glucose sensors), the initial rise of absorbance is sharp and the time until the absorbance becomes close to a constant value is short for any of the analytes of different Hct levels, although the content of enzyme (activity reference) in the reagent portion of the glucose sensors (1), (2) was lower than that in the glucose sensor (3) (comparative glucose sensor). This indicates that the use of the glucose sensors (1), (2) (inventive glucose sensors) can shorten the measurement time while reducing the amount of enzyme to be used. Particularly, in the glucose sensor (2) (inventive glucose sensor), the time course becomes stable in a shorter period of time (within five seconds) from the start of the measurement and the absorbance becomes close to a constant value more quickly than in the glucose sensor (1) (inventive glucose sensor). Therefore, to accurately measure the analyte of an unknown Hct level in a short time, the use of the glucose sensor (2) (inventive glucose sensor) is more preferable.

As will be understood from FIG. 17, as compared with the glucose sensor (3) (comparative glucose sensor), the bias of the five-second value in the glucose sensors (1) and (2) (inventive glucose sensors) is small with respect to both of the high-Hct analyte (60%) and the low-Hct analyte (20%), and the deviation from the intermediate-Hct analyte (42%) is small. This indicates that the glucose sensors (1), (2) are less likely to be influenced by the Hct level as compared with the glucose sensor (3) (comparative glucose sensor).

Example 2

Figure 18A:
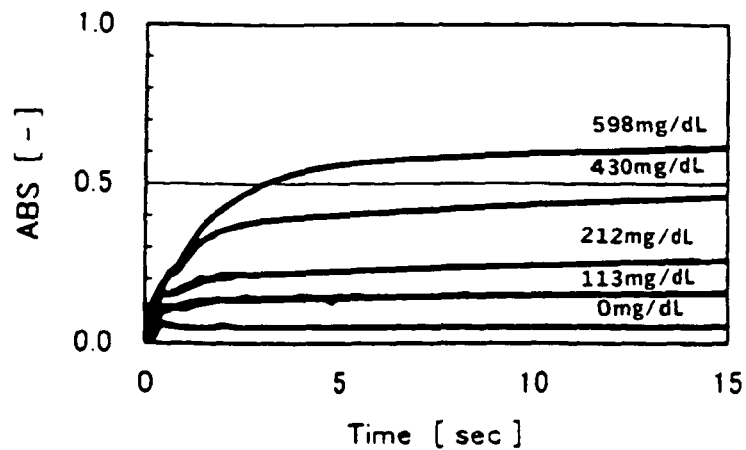
FIG. 18A is a graph showing the time course of absorbance measured using the glucose sensor (1) in Example 2.
Figure 18B:
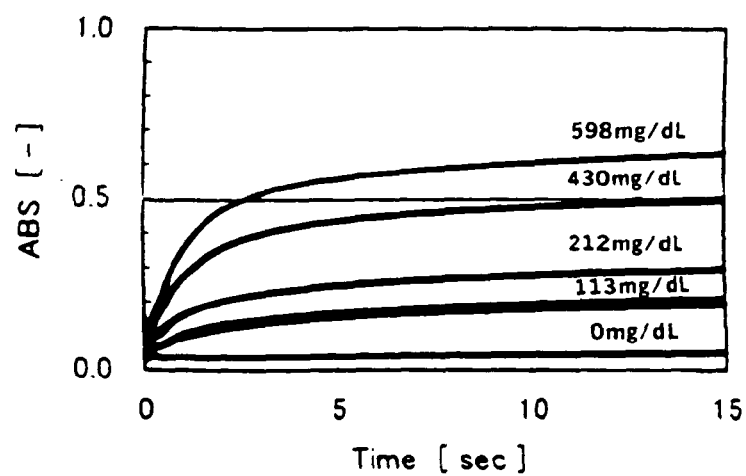
FIG. 18B is a graph showing the time course of absorbance measured using the glucose sensor (2) in Example 2.
Figure 18C:
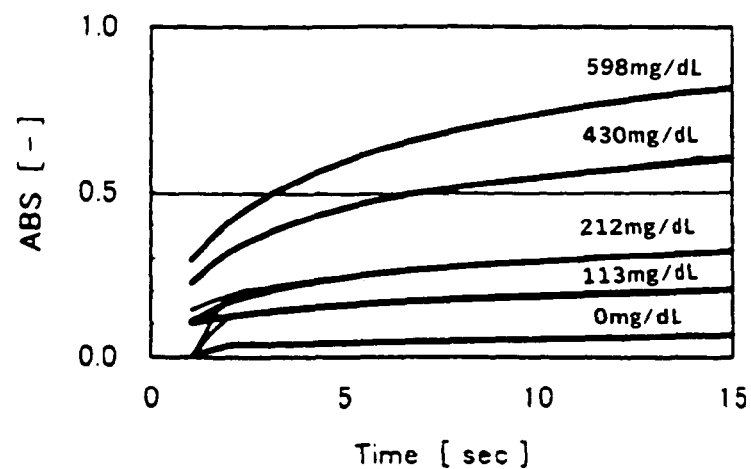
FIG. 18C is a graph showing the time course of absorbance measured using the glucose sensor (3) in Example 2.

In this example, the time course of absorbance of each of the glucose sensors (1)-(3), which were prepared similarly to Example 1, was measured using five kinds of analytes having different glucose levels (0 mg/dL, 113 mg/dL, 212 mg/dL, 430 mg/dL and 598 mg/dL). FIGS. 18A-18C show the results.

As will be understood from FIGS. 18A-18C, in the glucose sensors (1), (2) (inventive glucose sensors), the initial rise of absorbance is sharp and the time until the absorbance becomes close to a constant value is short for any of the analytes of different glucose levels, although the content of enzyme (activity reference) in the reagent portion of the glucose sensors (1), (2) was lower than that in the glucose sensor (3) (comparative glucose sensor). This also means that, as compared with the glucose sensor (3), the relationship between the absorbance and the glucose level in the glucose sensors (1), (2) has high linearity even when the measurement time is relatively short (e.g. within five seconds). Therefore, the glucose sensors (1), (2) can shorten the measurement time while covering a wide measurement range.

Example 3

The measurement reproducibility was evaluated based on the data obtained in Example 2. Specifically, the measurement reproducibility of each of the glucose sensors (1)-(3) was evaluated by computing the variations in the absorbance five seconds after the start of the measurement with respect to each of the analytes of different glucose levels. The computation results are given in Tables 8-10 below.

TABLE 8

Glucose Sensor (1): Inventive Glucose Sensor

| | Glucose Level | | | | |
|---|---|---|---|---|---|
| | 0 mg/dL | 113 mg/dL | 212 mg/dL | 430 mg/dL | 598 mg/dL |
| Absorbance | 0.051 | 0.140 | 0.228 | 0.395 | 0.500 |
| | 0.047 | 0.141 | 0.222 | 0.386 | 0.492 |
| | 0.051 | 0.141 | 0.224 | 0.388 | 0.558 |
| | 0.053 | 0.136 | 0.237 | 0.397 | 0.513 |
| | 0.056 | 0.143 | 0.209 | 0.385 | 0.475 |
| Average | 0.052 | 0.140 | 0.224 | 0.390 | 0.512 |
| S.D. | 0.00 | 0.00 | 0.01 | 0.00 | 0.03 |
| C.V. | 5.7% | 1.8% | 4.0% | 1.2% | 5.5% |

TABLE 9

Glucose Sensor (2): Inventive Glucose Sensor

| | Glucose Level | | | | |
|---|---|---|---|---|---|
| | 0 mg/dL | 113 mg/dL | 212 mg/dL | 430 mg/dL | 598 mg/dL |
| Absorbance | 0.041 | 0.174 | 0.254 | 0.451 | 0.575 |
| | 0.042 | 0.174 | 0.267 | 0.457 | 0.554 |
| | 0.036 | 0.170 | 0.271 | 0.468 | 0.557 |
| | 0.039 | 0.174 | 0.276 | 0.438 | 0.546 |
| | 0.046 | 0.165 | 0.270 | 0.455 | 0.535 |
| Average | 0.041 | 0.172 | 0.268 | 0.454 | 0.553 |
| S.D. | 0.00 | 0.00 | 0.01 | 0.01 | 0.01 |
| C.V. | 9.5% | 2.3% | 3.1% | 2.4% | 2.7% |

TABLE 10

Glucose Sensor (3): Comparative Glucose Sensor

| | Glucose Level | | | | |
|---|---|---|---|---|---|
| | 0 mg/dL | 113 mg/dL | 212 mg/dL | 430 mg/dL | 598 mg/dL |
| Absorbance | 0.044 | 0.160 | 0.246 | 0.453 | 0.592 |
| | 0.021 | 0.155 | 0.247 | 0.471 | 0.573 |
| | 0.030 | 0.139 | 0.243 | 0.483 | 0.620 |
| | 0.021 | 0.156 | 0.254 | 0.520 | 0.640 |
| | 0.016 | 0.157 | 0.264 | 0.493 | 0.613 |
| Average | 0.026 | 0.153 | 0.251 | 0.484 | 0.608 |
| S.D. | 0.01 | 0.01 | 0.01 | 0.02 | 0.02 |
| C.V. | 37.6% | 4.9% | 2.9% | 4.6% | 3.8% |

As will be understood from the Tables 8-10, in the glucose sensors (1), (2) (inventive glucose sensors), the C.V. (%) is generally low and the values itself is small as compared with those in the glucose sensor (3) (comparative glucose sensor), which means that the glucose sensors (1), (2) provide excellent reproducibility.

From the results of Examples 1-3, the following is concluded. When a first reagent portion 51A, 51B containing an electron mediator and a second reagent portion 52A, 52B containing a color former are separated from each other, and the first reagent portion 51A, 51B is arranged upstream from the second reagent portion 52A, 52B (glucose sensors (1), (2)), the influence of the Hct level can be reduced, and the measurement can be performed in a shorter period of time using a smaller amount of enzyme while covering a wide measurement range, as compared with the structure in which a second reagent portion 52C is arranged upstream from the first reagent portion 51C (glucose sensor (3)). Particularly, as compared with the structure in which the first reagent portion 51A contains both of an electron mediator and an oxidoreductase (glucose sensor (1)), the measurement time can be further shortened and the stability of measurement can be enhanced in the structure (glucose sensors (2)) in which the first reagent portion 51B containing an electron mediator and the third reagent portion 53B containing an oxidoreductase are separately provided and the first reagent portion 51B is positioned upstream from the third reagent portion 53B.

Example 4

Figure 19:
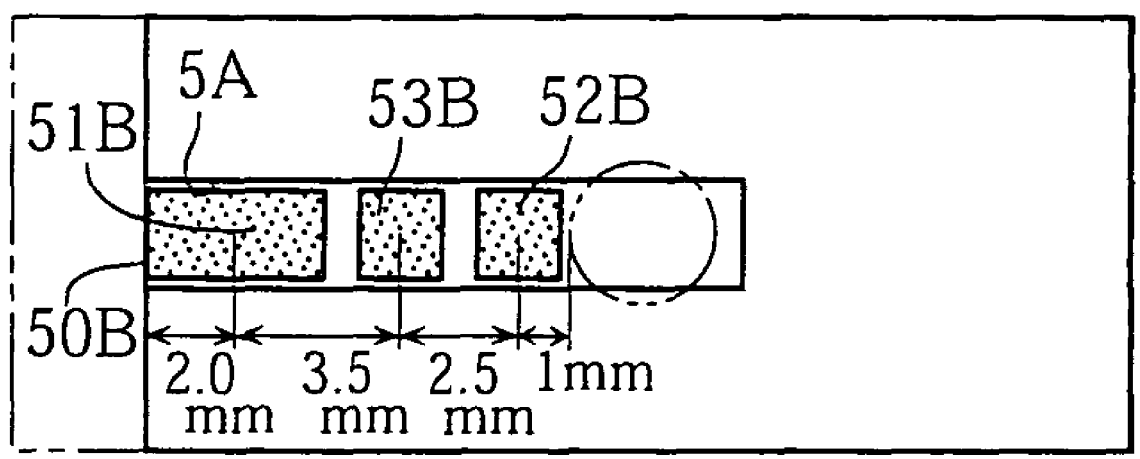
FIG. 19 is a plan view showing the structure of reagent portions in the inventive glucose sensor used in Example 4, with the transparent cover omitted.

In this Example, the measurement reproducibility was examined with respect to an inventive glucose sensor having the structure shown in FIG. 19 and a reference glucose sensor corresponding to the glucose sensor (2) of FIG. 15B.

The reference glucose sensor was prepared in a manner similar to the glucose sensor (2) of Example 1. The inventive glucose sensor was prepared in a manner similar to the reference glucose sensor (glucose sensor (2) of Example 1) except that the first reagent portion 51B' was formed by applying the same amount of liquid material having the same composition as the liquid material for forming the first reagent portion 51B, spreading the liquid material to an intended size and then drying the liquid material. Specifically, the first reagent portion 51B' of the inventive glucose sensor was formed to have a length of 3.5 mm which was longer than that of the third reagent portion 53B and to be thinner than the third reagent portion 53B. The length of the first reagent portion 51B' accounted for 87.5% of the distance from the introduction port 50B to the end of the third reagent portion 53B on the introduction portion 50B side.

The measurement reproducibility of the inventive glucose sensor and the reference glucose sensor was examined by measuring the time course of absorbance with respect to an analyte of 42% Hct in a manner similar to Example 1 and computing the variation of the absorbance value obtained five seconds after the start of the measurement. As the analyte, use was made of three kinds of analytes having different glucose levels (0 mg/dL, 100 mg/dL, 400 mg/dL). With respect to each of the glucose sensors, the time course was measured five times for the analyte of 0 mg/dL and ten times for the analytes of 100 mg/dL and 400 mg/dL.

Figure 20A:
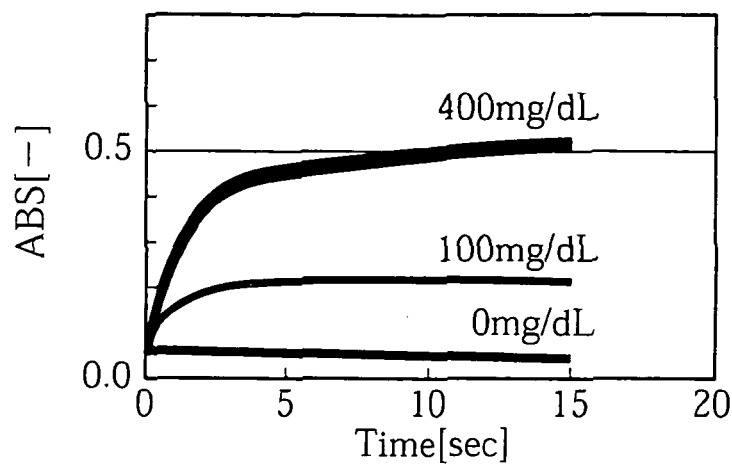
FIG. 20A is a graph showing the time course of absorbance measured at wavelength 660 nm using the inventive glucose sensor in Example 4.
Figure 20B:
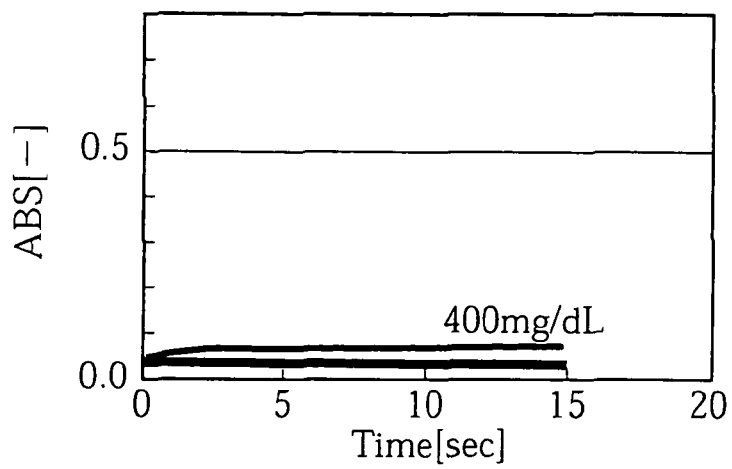
FIG. 20B is a graph showing the time course of absorbance measured at wavelength 940 nm using the inventive glucose sensor in Example 4.
Figure 20C:
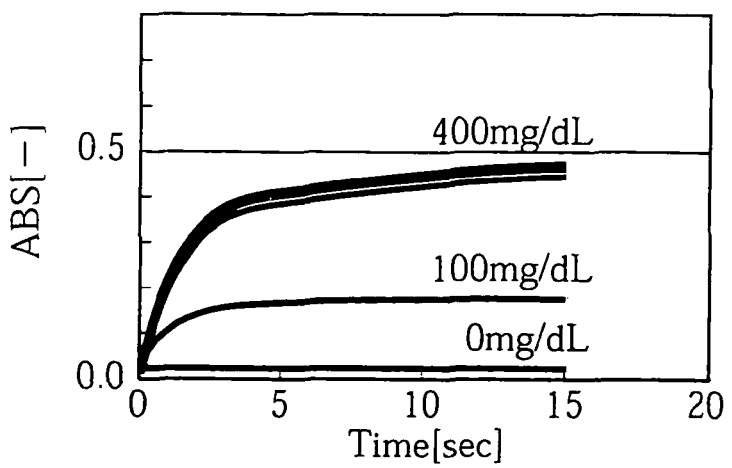
FIG. 20C is a graph showing the time course of absorbance of the inventive glucose sensor obtained by subtracting the measurements at wavelength 940 nm from the measurements at wavelength 660 nm.
Figure 21A:
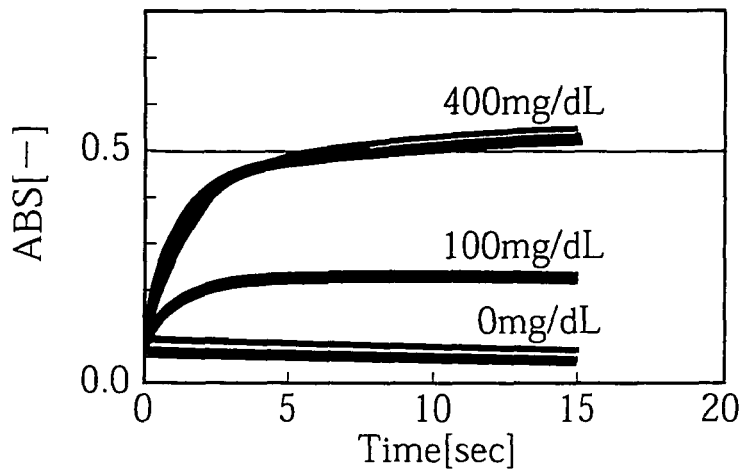
FIG. 21A is a graph showing the time course of absorbance measured at wavelength 660 nm using the reference glucose sensor in Example 4.
Figure 21B:
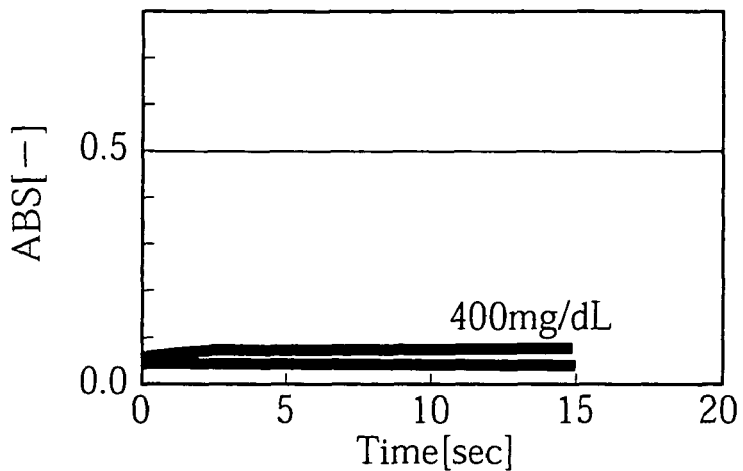
FIG. 21B is a graph showing the time course of absorbance measured at wavelength 940 nm using the reference glucose sensor in Example 4.
Figure 21C:
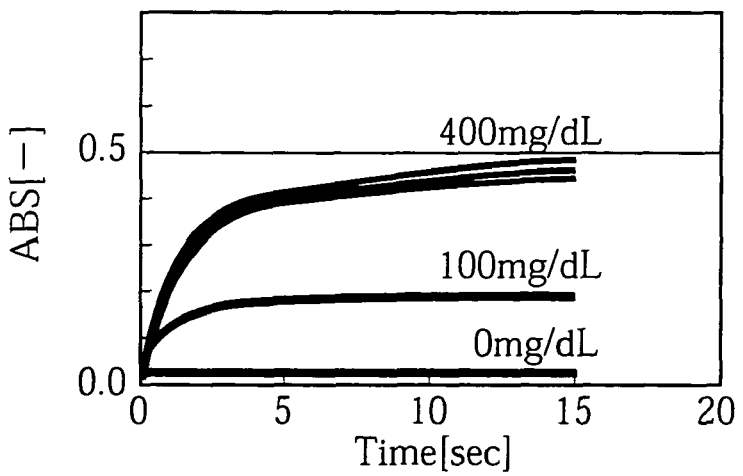
FIG. 21C is a graph showing the time course of absorbance of the reference glucose sensor obtained by subtracting the measurements at wavelength 940 nm from the measurements at wavelength 660 nm.

FIGS. 20A-20C show the time course of absorbance of the inventive glucose sensor, whereas FIGS. 21A-21C show that of the reference glucose sensor. The variations of absorbance in the inventive glucose sensor after five seconds are given in Table 11, whereas those in the reference glucose sensor are given in Table 12. Specifically, FIGS. 20A and 21A show the time courses measured using the light having a wavelength of 660 nm, FIGS. 20B and 21B show those measured using the light having a wavelength of 940 nm, and FIGS. 20C and 21C show those obtained by subtracting the measurements obtained using the light of wavelength 940 nm from the measurements obtained using the light of wavelength 660 nm. The variations of absorbance given in Tables 11 and 12 were those computed by subtracting the measurements obtained using the light of wavelength 940 nm from the measurements obtained using the light of wavelength 660 nm.

TABLE 11

Inventive Glucose Sensor

| | Glucose Level | | |
|---|---|---|---|
| | 0 mg/dL | 100 mg/dL | 400 mg/dL |
| Absorbance | 0.024 | 0.175 | 0.404 |
| | 0.024 | 0.174 | 0.405 |
| | 0.023 | 0.173 | 0.412 |
| | 0.023 | 0.174 | 0.411 |
| | 0.025 | 0.177 | 0.404 |
| | | 0.174 | 0.407 |
| | | 0.173 | 0.417 |
| | | 0.174 | 0.412 |
| | | 0.175 | 0.386 |
| | | 0.173 | 0.392 |
| Average | 0.024 | 0.174 | 0.405 |
| S.D. | 0.001 | 0.001 | 0.009 |
| C.V. | 4.0% | 0.7% | 2.3% |

TABLE 12

| | Reference Glucose Sensor | | |
| --- | --- | --- | --- |
| | Glucose Level | | |
| | 0 mg/dL | 100 mg/dL | 400 mg/dL |
| Absorbance | 0.027 | 0.180 | 0.419 |
| | 0.028 | 0.183 | 0.417 |
| | 0.026 | 0.184 | 0.421 |
| | 0.024 | 0.188 | 0.398 |
| | 0.034 | 0.182 | 0.414 |
| | | 0.184 | 0.412 |
| | | 0.188 | 0.409 |
| | | 0.184 | 0.407 |
| | | 0.187 | 0.403 |
| | | 0.182 | 0.406 |
| Average | 0.028 | 0.184 | 0.410 |
| S.D. | 0.004 | 0.003 | 0.007 |
| C.V. | 13.1% | 1.4% | 1.7% |

As will be understood from the comparison between FIGS. 20A-20C and FIGS. 21A-21C, the variations in time course of the absorbance in the inventive glucose sensor are clearly smaller than those of the reference glucose sensor. Further, as will be understood from the comparison between Table 11 and Table 12, as to the variations in absorbance after five seconds, the C.V. (%) in the low concentration range (not more than 100 mg/dL) is smaller in the inventive glucose sensor than in the reference glucose sensor. That is, as compared with the reference glucose sensor, the inventive glucose sensor is more excellent in the reproducibility in the low concentration range (not more than 100 mg/dL).

Herein, the reference glucose sensor corresponds to the glucose sensor (2) in Examples 1-3. The glucose sensor (2) is more excellent in reproducibility than the glucose sensors (1) and (3) in Examples 1-3. Therefore, the inventive glucose sensor is more excellent in reproducibility in the low concentration range than the glucose sensor (2) (reference glucose sensor) having excellent reproducibility.

Conceivably, this result is obtained because the first reagent portion 51B' of the inventive glucose sensor is thinly spread and hence has an enhanced solubility so that the variations of the concentration of the electron mediator in the sample introduced into the flow path is reduced. Therefore, it is concluded that, to enhance the reproducibility in a low concentration range, it is preferable to separate an electron mediator and an oxidoreductase and to improve the solubility of the electron mediator (diffusibility in the sample) by making the first reagent portion 51B' thin or longer than other reagent portions 52B, 53B in the sample flow direction.

The invention claimed is:

1. An analytical instrument having improved arrangement of reagent portion, the analytical instrument comprising:
a flow path for moving a sample containing blood cells;
an introduction port for introducing the sample into the flow path;
an electron detection medium for obtaining information necessary for analyzing an analysis target component contained in the sample in relation with an amount of electrons transferred;
a reagent portion arranged directly in the flow path, the reagent portion containing an electron mediator for supplying an electron taken from the analysis target component in the sample to the electron detection medium, at least part of the reagent portion being positioned adjacent to the introduction port; and
an additional reagent portion provided separately from said reagent portion and containing an oxidoreductase for taking an electron from the analysis target component contained in the sample and supplying the electron to the electron mediator;
wherein said reagent portion, the additional reagent portion, and the electron detection medium are provided on a same plane, and
the reagent portion is arranged upstream from the electron detection medium in a direction of flow of the sample while being separated from the electron detection medium.

2. The analytical instrument according to claim 1, wherein the reagent portion is in a solid state and dissolves when the sample is supplied to the flow path.

3. The analytical instrument according to claim 1, wherein the electron detection medium contains a color former.

4. The analytical instrument according to claim 3, wherein the electron detection medium is provided by causing a porous body which is sparingly soluble in the sample to support the color former.

5. The analytical instrument according to claim 1, wherein the electron detection medium comprises a conductor.

6. The analytical instrument according to claim 5, wherein the conductor is utilized for applying voltage to the electron mediator when the sample is supplied to the flow path.

7. The analytical instrument according to claim 1, wherein the reagent portion contains an oxidoreductase for taking an electron from the analysis target component contained in the sample and supplying the electron to the electron mediator.

8. The analytical instrument according to claim 7, wherein the oxidoreductase is glucose dehydrogenase (GDH).

9. The analytical instrument according to claim 8, wherein the oxidoreductase is PQQGDH, αGDH or CyGDH.

10. The analytical instrument according to claim 1, wherein the additional reagent portion is arranged between said reagent portion and the electron detection medium in a direction of flow of the sample in the flow path.

11. The analytical instrument according to claim 10, wherein said reagent portion is larger in area in plan view than the additional reagent portion.

12. The analytical instrument according to claim 10, wherein said reagent portion is larger than the additional reagent portion in length in the direction of flow of the sample.

13. The analytical instrument according to claim 10, wherein said reagent portion is smaller in thickness than the additional reagent portion.

14. The analytical instrument according to claim 13, wherein the thickness of said reagent portion is 15 to 80% of the thickness of the additional reagent portion.

15. The analytical instrument according to claim 10, wherein said reagent portion has an area in plan view which is 1.5 to 10 times an area in plan view of the electron detection medium in the flow path.

16. The analytical instrument according to claim 10, wherein said reagent portion has a length which accounts for 50 to 90% of distance from the sample introduction port to an end of the additional reagent portion on the sample introduction port side.

17. The analytical instrument according to claim 10, wherein said reagent portion and the additional reagent portion are designed to dissolve when the sample is introduced into the flow path.

18. The analytical instrument according to claim 1, wherein the electron mediator is a Ru complex.

19. The analytical instrument according to claim 1, wherein the analysis target component in the sample is glucose.

20. The analytical instrument according to claim 1, wherein the flow path is designed to generate a capillary force.

21. An analytical instrument having improved arrangement of reagent portion, the analytical instrument comprising:
   a flow path for moving a sample containing blood cells;
   an introduction port for introducing the sample into the flow path;
   a reagent portion arranged in the flow path; and
   an electron detection medium for obtaining information necessary for analyzing an analysis target component contained in the sample in relation with an amount of electrons transferred;
   wherein the reagent portion contains an electron mediator for supplying an electron taken from the analysis target component in the sample to the electron detection medium, and at least part of the reagent portion is positioned adjacent to the introduction port,
   wherein the reagent portion is arranged upstream from the electron detection medium in a direction of flow of the sample while being separated from the electron detection medium,
   wherein the reagent portion is in a solid state and dissolves when the sample is supplied to the flow path,
   wherein center-to-center distance between the reagent portion and the electron detection medium is so set that, when the sample contains the analysis target component in maximum amount of a predetermined detection range, electron transfer from the maximum amount of analysis target component to the electron mediator is substantially completed before the electron mediator becomes able to supply electrons to the electron detection medium.

22. An analytical instrument having improved arrangement of reagent portion, the analytical instrument comprising:
   a flow path for moving a sample containing blood cells;
   an introduction port for introducing the sample into the flow path;
   a reagent portion arranged in the flow path; and
   an electron detection medium for obtaining information necessary for analyzing an analysis target component contained in the sample in relation with an amount of electrons transferred;
   wherein the reagent portion contains an electron mediator for supplying an electron taken from the analysis target component in the sample to the electron detection medium, and wherein at least part of the reagent portion is positioned adjacent to the introduction port,
   wherein the reagent portion is arranged upstream from the electron detection medium in a direction of flow of the sample while being separated from the electron detection medium,
   wherein the reagent portion is in a solid state and dissolves when the sample is supplied to the flow path,
   wherein the content of the electron mediator in the reagent portion is so set that, when the sample contains the analysis target component in maximum amount of a predetermined detection range, the electron mediator can receive all the electrons taken from the maximum amount of analysis target component.

* * * * *